United States Patent [19]
Ohno et al.

[11] Patent Number: 5,367,078
[45] Date of Patent: Nov. 22, 1994

[54] 3-OXADIAZOLYL-1,6-NAPHTHYRIDINE DERIVATIVES

[75] Inventors: Kazunori Ohno, Higashiosaka; Osamu Odai, Takatsuki; Yukio Tominaga, Toyonaka; Kiyoshi Furukawa, Shiga; Makoto Oka, Ibaraki, all of Japan

[73] Assignee: Dainippon Pharmaceutical Co., Ltd., Osaka, Japan

[21] Appl. No.: 112,660

[22] Filed: Aug. 27, 1993

[30] Foreign Application Priority Data

Sep. 2, 1992 [JP] Japan ................................ 4-260796
Apr. 28, 1993 [JP] Japan ................................ 5-124964

[51] Int. Cl.$^5$ ................................................ C07D 471/04
[52] U.S. Cl. ................................................... 546/122
[58] Field of Search ..................................... 546/122

[56] References Cited

U.S. PATENT DOCUMENTS 3,555,034  1/1971  Diebold et al. ........................ 546/121

OTHER PUBLICATIONS

W. Roger Tully, "2-(Oxadiazolyl)-and 2-(Thiazolyl)imidazo[1,2-a]pyrimidines as Agonists and Inverse Agonists at Benzodiazepine Receptors", J. Med. Chem. 1991, 34, pp. 2060-2067.

Nguyen Chau, "Synthesis of Substituted N-2,4-Dioxo-1,2,3,4-tetrahydroquinazolinyl)benzamides and N-(-2-Thiono-4-oxo-1,2,3,4-tetrahydroquinazolinyl)benzamides", J. Heterocyclic Chem., 19, 541 (1982).

R. K. Tewari, "Synthesis of some New Mannich Bases, Sulphides and Disulphides of 1,3,4-Oxadiazol-2-thiones as Potential Antifungal Agents", J. Indian Chem. Soc., vol. 68, Feb. 1991.

Lawrence L. Whitfield, "Heterocycles from N-Benzolthioamides and Dinucelophilic Reagents", J. Heterocyclic Chem., 18, 1197 (1981).

P. Molina, "Iminophosphorane-Mediated Synthesis of 3,5-Disubstituted 1,2,4-Oxadiazoles", Synthesis, 843 (1986).

Frank Haglid, "Syntheses of tetrahydronaphthyridines", Chemical Abstracts, vol. 67, 1967.

Kou-Chang Liu, "A Particularly Convenient Preparation of Benzohydroximinoyl Chlorides (Nitrile Oxide Precursors)", J. Org. Chem. 1980, 45, pp. 3916-3918.

Haukur Kristinsson, "Synthese von Heterocyclen; IV. Neuer Syntheseweg zur Herstellung von Heterocyclischen Nitrilen", Synthesis, 102(1979).

Gilbert Stork, "The Enamine Alkylation and Acylation of Carbonyl Compounds", JACS 85, 207 (1963).

R. A. Olofson, "A New Reagent for the Selective, High-Yield N-Dealkylation of Tertiary Amines: Improved Syntheses of Naltrexone and Nalbuphine", J. Org. Chem. 1984, 49, pp. 2081-2082.

Hanns Mohler, "Properties of $^3$H-Diazepam Binding to Benzodiazepine Receptors in Rat Cerebral Cortex", Life Sciences vol. 20, pp. 2101-2110, 1977.

E. A. Swinyard, "Assay of Antiepileptic Drug Activity in Experimental Animals: Standard Tests"; Anticonvulsant Drugs, Mercier, J., Ed., pp. 47-65, Pergamon Press, New York, 1973.

*Primary Examiner*—Bernard Dentz
*Attorney, Agent, or Firm*—Wenderoth, Lind & Ponack

[57] ABSTRACT

3-Oxadiazolyl-5,6,7,8-tetrahydro-1,6-naphthyridine derivative of the formula (I):

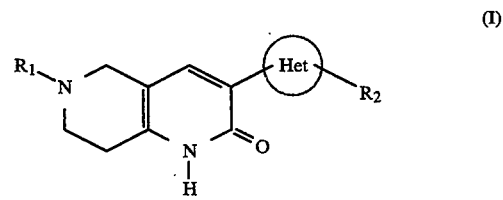

wherein Het is an oxadiazole ring, $R_1$ is hydrogen atom, an acyl group, a lower alkyl group or a group of the formula: —$CH_2R_1'$ (in which $R_1'$ is a cyclo-lower alkyl group, a lower alkenyl group, a lower alkynyl group, benzyl group, aryl group or a heteroaromatic groups), $R_2$ is a lower alkyl group, a cyclo-lower alkyl group, a lower alkenyl group, a lower alkynyl group, aryl group, a heteroaromatic group, a halogeno-lower alkyl group, a lower alkoxy-lower alkyl group, a lower alkoxy group, a lower alkenyloxy group, a phenoxy group, or a lower alkylthio group, or a pharmaceutically acceptable acid addition salt thereof, which are useful as benzodiazedine receptor agonist.

18 Claims, No Drawings

3-OXADIAZOLYL-1,6-NAPHTHYRIDINE DERIVATIVES

The present invention relates to a 3-oxadiazolyl-5,6,7,8-tetrahydro-1,6-naphthyridine derivative which is useful as a medicine, a process for preparing the same, use of the same as a medicine, and an intermediate thereof.

PRIOR ART

Benzodiazepine (BZP) compounds such as diazepam have widely been used as anxiolytic drug or in the treatment of insomnia. However, these compounds show various side effects such as ataxia, sleepiness, muscular relaxation, or deterioration of recognition or reflex movement, and they also have various defects, for example, they cause drug-resistance or drug-dependence in patients. In order to solve these problems, there has been studied non-benzodiazepine compounds have affinity for BZP receptor in brain.

As one of these non-benzodiazepine compounds those having the following formulae are disclosed in Journal of Medicinal Chemistry, Vol. 34, p. 2060 (1991).

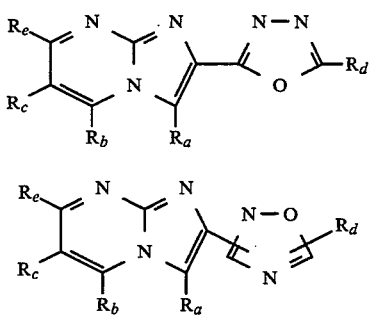

where $R_a$ is hydrogen atom, $R_b$ to $R_d$ are methyl group, etc., and $R_e$ is methoxy group, etc.

However, there have never been disclosed the compounds of the formula (I) of the present invention.

BRIEF DESCRIPTION OF THE INVENTION

An object of the present invention is to provide a 3-oxadiazolyl-5,6,7,8-tetrahydro-1,6-naphthyridine derivative of the following formula (I) or a pharmaceutically acceptable acid addition salt thereof, which have an affinity for benzodiazepine receptor and are useful as a medicine.

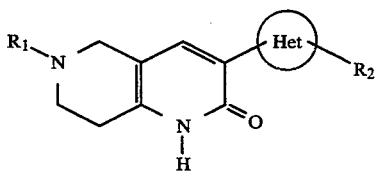

(I)

wherein Het is an oxadiazole ring, $R_1$ is hydrogen atom, an acyl group, a lower alkyl group or a group of the formula: —$CH_2R_1'$ (in which $R_1'$ is a cyclo-lower alkyl group, a lower alkenyl group, a lower alkynyl group, benzyl group, an aryl group or a heteroaromatic group), $R_2$ is a lower alkyl group, a cyclo-lower alkyl group, a lower alkenyl group, a lower alkynyl group, an aryl group, a heteroaromatic group, a halogeno-lower alkyl group, a lower alkoxy-lower alkyl group, a lower alkoxy group, a lower alkenyloxy group, a phenoxy group or a lower alkylthio group.

Another object of the invention is to provide a process for preparing the compound of the formula (I).

A further object of the invention is to provide a pharmaceutical composition containing said compound as an active ingredient, and also use thereof as a medicine.

Still further object of the invention is to provide a synthetic intermediate for preparing the compound of the formula (I).

DETAILED DESCRIPTION OF THE INVENTION

The compounds of the present invention have the above formula (I), but are more preferably compounds of the formula (I) wherein Het is 1,2,4-oxadiazole ring or 1,3,4-oxadiazole ring, $R_1$ is a group of the formula: —$CH_2R_1'$, $R_1'$ is an aryl group or a heteroaromatic group, $R_2$ is a lower alkyl group, a cyclo-lower alkyl group, a lower alkenyl group, an aryl group, a heteroaromatic group or a lower alkoxy group. Particularly preferable compounds of the present invention are compounds of the formula (I) wherein Het is 1,3,4-oxadiazole ring, $R_1$ is a group of the formula: —$CH_2R_1'$, $R_1'$ is phenyl group or a phenyl group substituted by 1 to 2 halogen atoms, $R_2$ is an alkyl group having 2 to 3 carbon atoms, cyclopropyl group or methoxy group.

Throughout the present description and claims, the "lower alkyl", "lower alkoxy" and "lower alkylthio" denote straight chain or branched chain alkyl, alkoxy and alkylthio having 1 to 5 carbon atoms, respectively. The "lower alkenyl", "lower alkynyl" and "lower alkenyloxy" denote straight chain or branched chain alkenyl, alkynyl, and alkenyloxy having 2 to 5 carbon atoms, respectively. The "cyclo-lower alkyl" denotes a cycloalkyl having 3 to 6 carbon atoms. The "acyl" denotes a straight chain or branched chain alkanoyl having 1 to 5 carbon atoms, benzoyl, naphthoyl, etc. The "aryl group" denotes, for example, phenyl group, naphthyl group, and the like, and these groups may optionally have 1 to 3 substituents selected from a halogen atom, a lower alkyl group, trifluoromethyl group, a lower alkoxy group and nitro group. The "heteroaromatic group" includes a 5- or 6-membered heteroaromatic group containing 1 to 2 heteroatoms selected from nitrogen atom, oxygen atom, sulfur atom, for example, thienyl, furyl, pyridinyl, isoxazolyl, and the like, and these heteroaromatic groups may optionally have 1 to 3 substituents selected from a halogen atom, a lower alkyl group, trifluoromethyl group, a lower alkoxy group.

The pharmaceutically acceptable acid addition salts of the compounds (I) are, for example, salts with an inorganic acid (e.g. hydrochloride, hydrobromide, hydroiodide, sulfate, phosphate, etc.) or salts with an organic acid (e.g. oxalate, maleate, fumarate, malonate, lactate, realate, citrate, tartrate, benzoate, methanesulfonate, tosylate, etc.).

The compounds of the present invention can be prepared by various processes as mentioned below.

Process 1

Among the compounds (I) of the present invention, the compound of the formula (Ia):

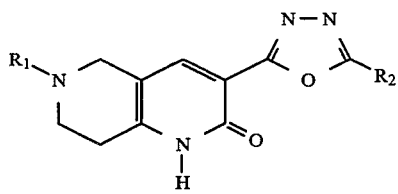

(Ia)

wherein $R_1$ is the same as defined above, and $R_2$ is groups other than a lower alkylthio group can be prepared by subjecting a compound of the formula (II):

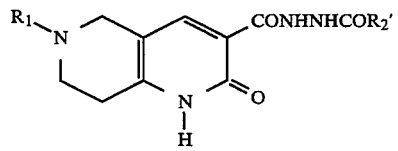

(II)

wherein $R_2'$ is the same as $R_2$ except a lower alkylthio group, and $R_1$ is the same as defined above, to intramolecular cyclodehydration.

This cyclization reaction is usually carried out by treating the compound (II) with a dehydrating agent. The dehydrating agent is, for example, a combination of a phosphorus (III) compound (e.g. triphenylphosphine, etc.) and a dialkyl azodicarboxylate, or a phosphorus (V) compound (e.g. polyphosphoric acid, phosphorus oxychloride, etc.), and the like, but preferable one is a combination of a phosphorus (III) compound and a dialkyl azodicarboxylate. The reaction may be carried out in a solvent or without a solvent, but usually carried out in an inert solvent which does not affect the reaction. The solvent includes, for example, ethers (e.g. tetrahydrofuran, dioxane, etc.), aromatic hydrocarbons (e.g. benzene, toluene, etc.), halogenated hydrocarbons (e.g. dichloromethane, chloroform, etc.), and the like. These solvents can be used either alone or in a mixture of two or more solvents. When the reaction is carried out by using a combination of a phosphorus (III) compound and a dialkyl azodicarboxylate, the reaction is preferably carried out in the presence of a base. The base includes organic bases such as triethylamine, tributylamine, diisopropylamine, N-methylmorpholine, pyridine, and the like. The reaction temperature varies according to the types of the starting compound, but is usually in a range of 0° C. to 110° C., preferably in a range of 0° C. to 70° C. When the compound of the formula (II) wherein $R_1$ is hydrogen atom is used in the reaction, the compound (II) may be protected by a suitable protecting group which can be removed after the cyclization reaction. The protecting group is, for example, a lower alkanoyl group (e.g. formyl group, acetyl group, etc.), a lower alkoxycarbonyl group and benzyloxycarbonyl group. The cyclization reaction with a phosphorus (III) compound and a dialkyl azodicarboxylate is a novel reaction.

Process 2

Among the compounds (I) of the present invention, the compound of the formula (I) wherein $R_2$ is a lower alkylthio group can be prepared by a process as shown in the following reaction scheme.

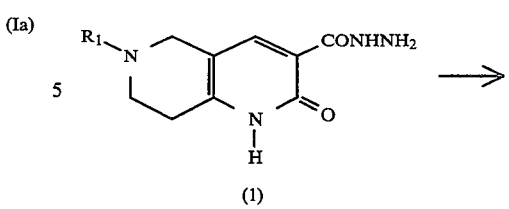

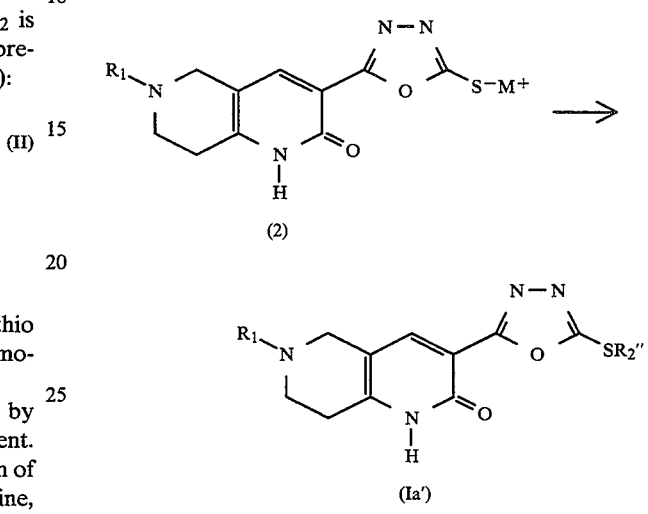

wherein $R_2''$ is a lower alkyl group, M is sodium or potassium, and $R_1$ is the same as defined above.

The compound (1) is reacted with carbon disulfide in the presence of a base according to the method disclosed in Journal of Heterocyclic Chemistry, Vol. 19, p. 541 (1982) to give the compound (2), and then, the compound (2) is reacted with an alkylating agent (e.g. a lower alkyl halide, etc.) according to the method disclosed in Journal of Indian Chemical Society, Vol. 68, p. 108 (1991) to give the compound (1a') which is a compound of the formula (1a) wherein $R_2$ is a lower alkylthio group. When $R_1$ in the compound (I) is hydrogen atom, it may be protected by a suitable protecting group, which may be removed after the reaction, like is the above Process 1.

Process 3

Among the compounds (I) of the present invention, the compound of the formula (Ib):

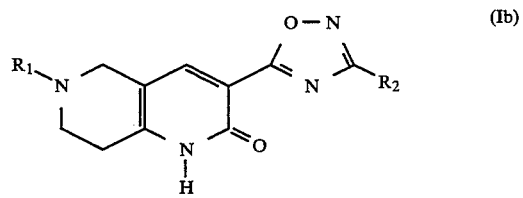

(Ib)

wherein $R_2$ is groups other than a lower alkoxy group, a lower alkenyloxy group, phenoxy group and a lower alkylthio group and $R_1$ is the same as defined above;, can be prepared by subjecting a compound of the formula (III):

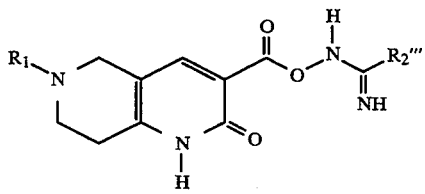

(III)

wherein $R_2'''$ is the same groups other than a lower alkoxy group, a lower alkenyloxy group, phenoxy group and a lower alkylthio group as defined for $R_2$, and $R_1$ is the same as defined above, to intramolecular cyclodehydration.

Besides, among the compounds (I) of the present invention, the compound of the formula (Ic):

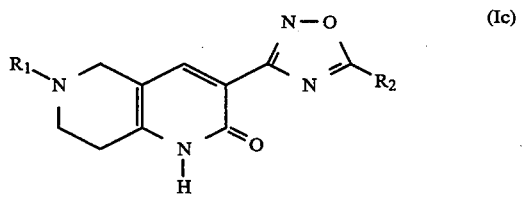

(Ic)

wherein $R_2$ is groups other than a lower alkoxy group, a lower alkenyloxy group, phenoxy group and a lower alkylthio group, and $R_1$ is the same as defined above, can be prepared by subjecting a compound of the formula (IV):

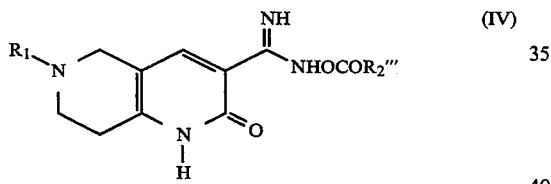

(IV)

wherein $R_1$ and $R_2'''$ are the same as defined above, to intramolecular cyclodehydration.

The cyclization reaction of the compound (III) and the compound (IV) can be carried out by treating said compounds with a dehydrating agent, usually with heating in a suitable solvent which does, not affect the reaction. The solvent includes, for example, aromatic hydrocarbons (e.g. benzene, toluene, xylene, etc.), ethers (e.g. tetrahydrofuran, dioxane, etc.), and the like. These solvents may be used either alone or in a mixture of one or more solvents. The reaction temperature varies according to the types of the starting compound, but it is usually in a range of 50° C. to 150° C., preferably in a range of 80° C. to 120° C. When the compound (III) and the compound (IV) wherein $R_1$ is hydrogen atom are used in these reactions, the compound (III) and the compound (IV) may be protected by a suitable protecting group, which can be removed after the cyclization reaction. The protecting group includes, for example, a lower alkanoyl group (e.g. formyl group, acetyl group, etc.), a lower alkoxycarbonyl group and benzyloxycarbonyl group.

Process 4

Among the compounds (I) of the present invention, the compounds of the formula (Ib) wherein $R_2$ is a lower alkoxy group, a lower alkenyloxy group, phenoxy group or a lower alkylthio group and $R_1$ is the same as defined above can be prepared by reacting a compound of the formula (V):

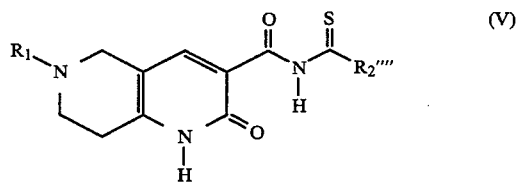

(V)

wherein $R_2''''$ is a lower alkoxy group, a lower alkenyloxy group, phenoxy group or a lower alkylthio group, and $R_1$ is the same as defined above, with hydroxylamine according to the method disclosed in Journal of Heterocyclic Chemistry, Vol. 18, p. 1197 (1981).

The reaction is usually carried out in a suitable solvent, for example, alcohols (e.g. methanol, ethanol, etc.), water, and the like. The reaction temperature varies according to the types of the staffing compound, but it is usually in a range of 50° C. to 90° C.

Process 5

Among the compounds (I) of the present invention, the compounds of the formula (Ic) wherein $R_2$ is a lower alkoxy group, a lower alkenyloxy group, phenoxy group or a lower alkylthio group and $R_1$ is the same as defined above can be prepared according to the method disclosed in Synthesis, p. 843 (1986), that is, by subjecting a compound of the formula (VI):

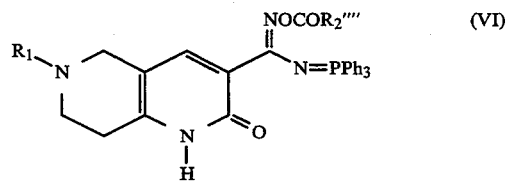

(VI)

wherein $R_1$ and $R_2''''$ are the same as defined above and Ph means phenyl group, to intramolecular cyclization.

The cyclization reaction is carried out by heating in a suitable solvent, for example, aromatic hydrocarbons (e.g. benzene, toluene, xylene, etc.) and ethers (e.g. tetrahydrofuran, dioxane, etc.). The reaction temperature varies according to the types of the starting compound, but it is usually in a range of 50° C. to 150° C., preferably 80° C. to 120° C.

The present compounds (I) prepared by the above mentioned processes 1 to 5 are isolated and purified by a conventional method such as chromatography, recrystallization, reprecipitation, and the like.

The compounds (I) of the present invention are obtained either in a free form or in the form of an acid addition salt thereof, depending on the types of the starting compound to be used, on the reaction conditions, and the like. The acid addition salt can be converted into a free base by a conventional method, for example, by treating it with a base such as alkali metal carbonates, alkaline earth metal carbonates, alkali metal hydroxides, alkaline earth metal hydroxides, etc. The free base can be converted into an acid addition salt thereof by a conventional method, for example, treating it with an inorganic or organic acid.

Process for preparing the starting compound

The compounds (II) used in the above mentioned Process 1 are a novel compound, and can be prepared by a process as shown in the following reaction scheme.

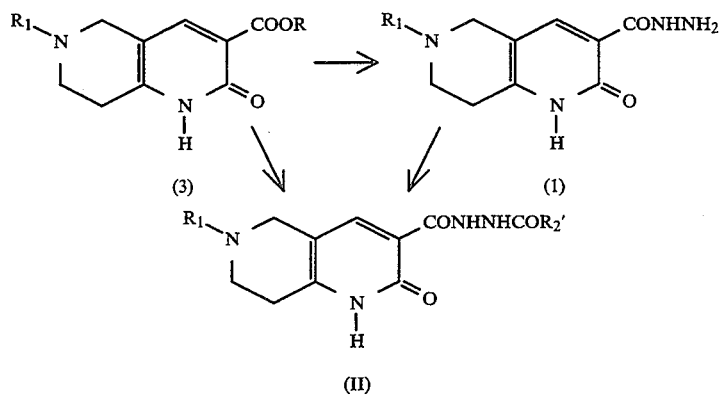

wherein R is hydrogen atom or a lower alkyl group, and $R_1$ and $R_2'$ are the same as defined above.

The synthesis of the compound (II) from the compound (3) is carried out by reacting the compound (3) or a reactive derivative at the carboxyl group thereof with a hydrazide compound of the formula: $H_2NNHCOR_2'$ ($R_2'$ is the same as defined above) by a conventional amidation reaction.

Alternatively, the compounds (II) may also be prepared by two steps, that is, by reacting the compound (3) or a reactive derivative at the carboxyl group thereof with hydrazine by a conventional amidation reaction, followed by acylating the product with a reactive derivative of a carboxylic acid of the formula: $R_2'COOH$.

The compound (3) is prepared according to the method disclosed in Arkiv foer Kemi 26 (41), pp. 489–495 (1967) [Chemical Abstract Vol. 67, 32611z (1967)], or may also be prepared by other various processes as described hereinafter.

The compounds (III) used in Process 3 are a novel compound, and prepared by a process as shown in the following reaction scheme.

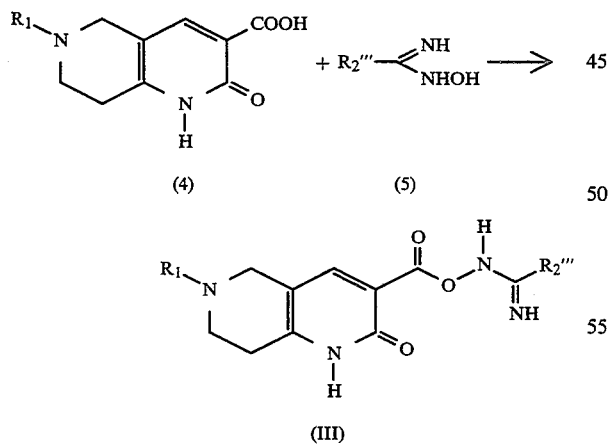

wherein $R_1$ and $R_2'''$ are the same as defined above.

The compound (III) is prepared by reacting the compound (4) or a reactive derivative at the carboxyl group thereof with an amidoxime (5) under the conditions for a conventional amidation reaction. When $R_1$ in the compound (4) is hydrogen atom, the compound (4) may be protected by a protecting group as mentioned hereinbefore.

The compounds (IV) prepared by Process 3 are also a novel compound, and prepared by a process as shown in the following reaction scheme.

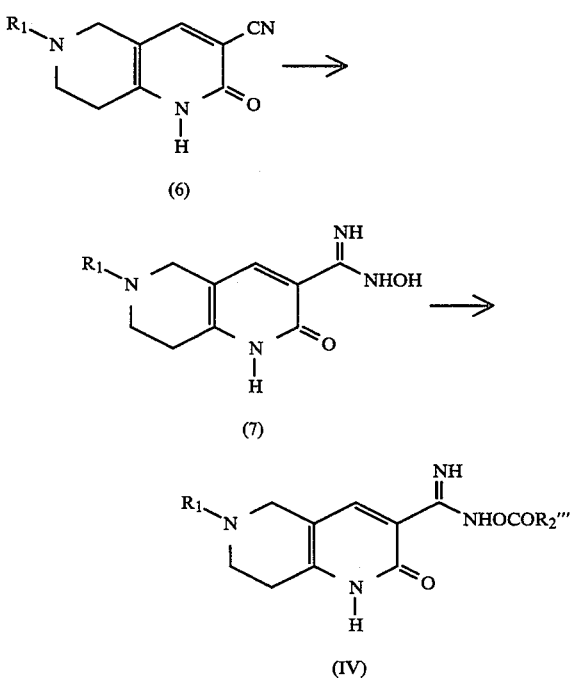

wherein $R_1$ and $R_2'''$ are the same as defined above.

The compound (6) is reacted with hydroxylamine by a conventional method to give the compound (7), which is further reacted with a reactive derivative at the carboxyl group of a carboxylic acid of the formula: $R_2'''COOH$ ($R_2'''$ is the same as defined above) in the presence of a base to give the compound (IV). When the compound (7) wherein $R_1$ is hydrogen atom is used, the $R_1$ group may be protected by a protecting group as mentioned hereinbefore.

The compound (V) used in Process 4 is prepared by a process as shown in the following reaction scheme.

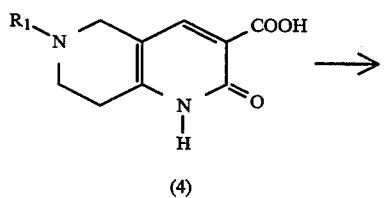

(4)

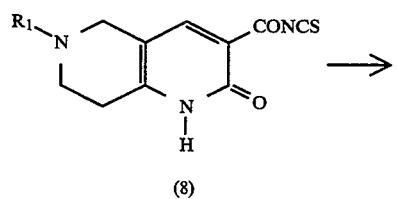

(8)

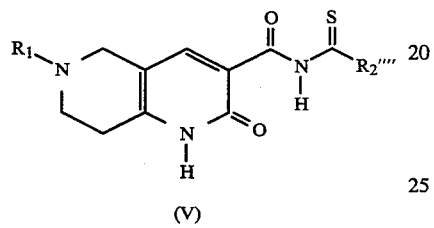

(V)

wherein R₁ and R₂'''' are the same as defined above.

The compound (4) or a reactive derivative at the carboxyl group thereof is reacted with an alkali metal salt or ammonium salt of thiocyanic acid in a suitable solvent to give the compound (8), which is further subjected to alcoholysis, or alternatively, treated with a lower alkylthiol or a alkali metal salt thereof in a suitable solvent, to give the compound (V). When the compound (8) wherein R₁ is hydrogen atom is used, the R₁ group may be protected with a protecting group as mentioned hereinbefore.

The compound (VI) used in Process 5 is a novel compound, and prepared by a method as shown in the following reaction scheme.

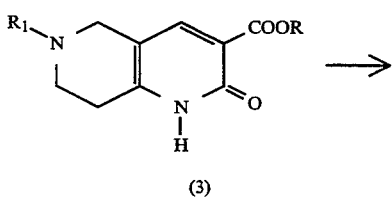

(3)

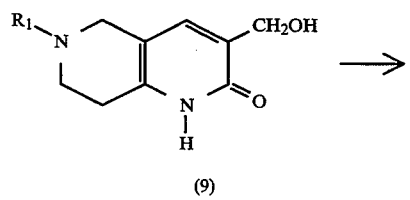

(9)

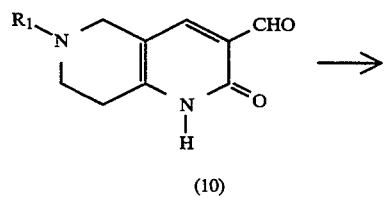

(10)

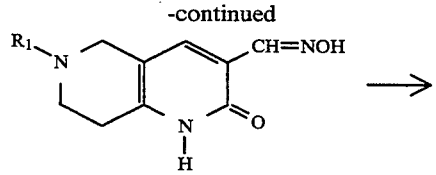

(11)

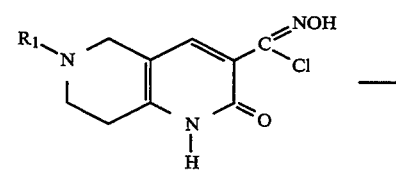

(12)

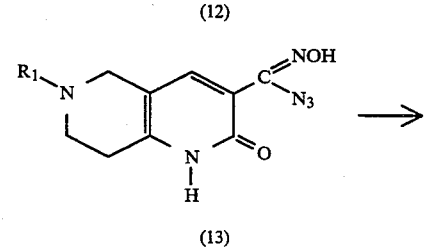

(13)

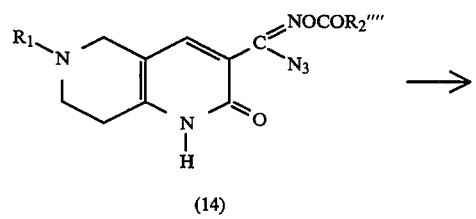

(14)

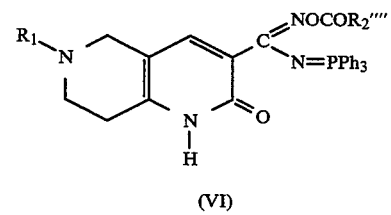

(VI)

wherein R, R₁ and R₂'''' are the same as defined above, and Ph means phenyl group.

The compound (3) is reduced with a reducing agent such as sodium borohydride, tetrabutylammonium borohydride, lithium aluminum hydride in a suitable solvent which does not affect the reaction to give the compound (9), which is further subjected to oxidation with active manganese dioxide in a suitable solvent to give the compound (10).

The compound (10) is reacted with hydroxylamine under the conditions for a conventional oxime forming reaction to give the compound (11), which is reacted with N-chlorosuccinimide according to the method disclosed in Journal of Organic Chemistry, Vol. 45, p. 3916 (1980) to give the compound (12).

The compound (12) is reacted with sodium azide in a suitable solvent according to the method disclosed in Synthesis, p. 102 (1979) to give the compound (13).

The compound (13) is reacted with a haloformic acid ester or a reactive derivative of S-lower alkylthiocarboxylic acid ester in a suitable solvent according to the method disclosed in Synthesis, p. 843 (1986) to give the compound (14), which is further reacted with triphenylphosphine to give the compound (VI).

The compound (12) can also be prepared according to the method disclosed in Synthesis, p. 102 (1979) as shown in the following reaction scheme.

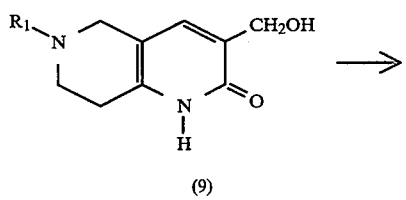
(9)

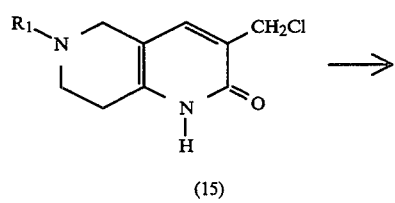
(15)

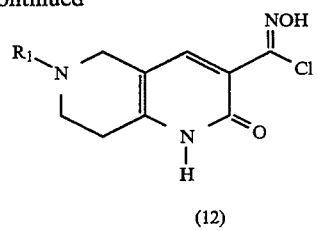
(12)

wherein $R_1$ is the same as defined above.

The compound (9) is reacted with a phosphorus compound (e.g. phosphorus trichloride, phosphorus oxychloride, etc.) or a thionyl chloride in a suitable solvent to give the compound (15), which is further reacted with an alkyl nitrite in the presence of an acid in a suitable solvent to give the compound (12).

The compound (3), compound (4) and compound (6), which are converted into the compounds (II)–(VI), are prepared according to the method disclosed in Arkiv foer Kemi 26 (41), 489–495 (1967) [Chemical Abstract Vol. 67, 32611z (1967)], or prepared by a process as shown in the following reaction scheme.

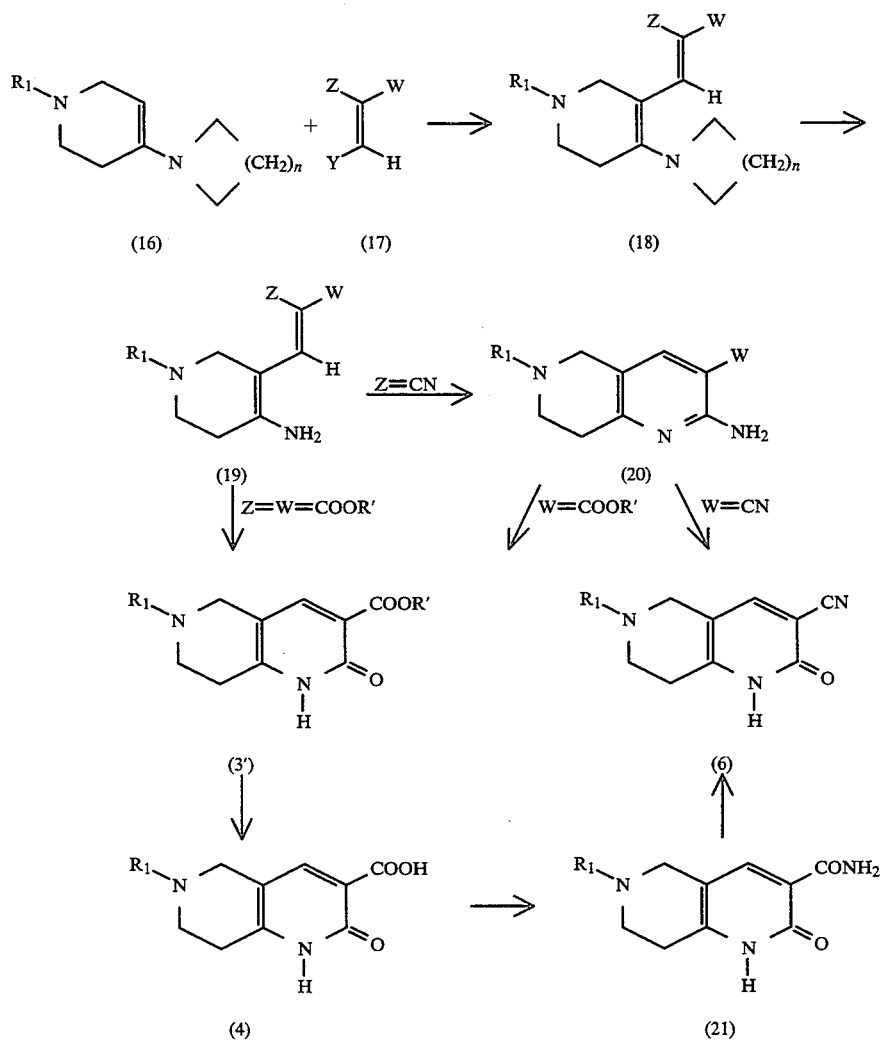

wherein Y is a halogen atom, a lower alkoxy group or a di-lower alkylamino group, W and Z are the same or different and each cyano group or a lower alkoxycarbonyl group, R' is a lower alkyl group, n is an integer of 1 to 3, and $R_1$ is the same as defined above.

The starting compound (16) in the above reaction scheme can be prepared according to the method disclosed in Journal of American Chemical Society, Vol. 85, p. 207 (1963). The compound (16) thus prepared is reacted with the compound (17) in a solvent such as alcohols (e.g. methanol, ethanol, etc.), ethers (e.g. tetrahydrofuran, dioxane, etc.), aromatic hydrocarbons (e.g. benzene, toluene, etc.) at a temperature from 0° C. to 120° C. to give the compound (18), which is further reacted with ammonia or an ammonium salt (e.g. ammonium acetate, etc.) in a solvent such as alcohols (e.g. methanol, ethanol, etc.), ethers (e.g. tetrahydrofuran, dioxane, etc.) and acetonitrile at a temperature from 0° C. to 100° C. to give the compound (19).

When both W and Z in the compound (19) are a lower alkoxycarbonyl group, the compound (19) is heated in a solvent such as alcohols (e.g. methanol, ethanol, etc.), ethers (e.g. tetrahydrofuran, dioxane, etc.) and aromatic hydrocarbons (e.g. benzene, toluene, xylene, etc.) at a temperature from 50° C. to 120° C. to give the compound (3'), which is further hydrolyzed under an acidic or basic condition by a conventional method to give the compound (4).

When in the compound (19) Z is cyano group, the compound (19) is treated in the presence of a base in a suitable solvent such as alcohols (e.g. methanol, ethanol, etc.), ethers (e.g. tetrahydrofuran, dioxane, etc.) and the like, at a temperature from 0° C. to 100° C. to give the compound (20), which is further reacted with sodium nitrite under an acidic condition, for example, in 5 to 10% aqueous hydrochloric acid solution or 5 to 20% aqueous sulfuric acid solution, at a temperature from 0° C. to 20° C. to give the compound (3') when W in the compound (20) is an ester group, or the compound (6) when W in the compound (20) is cyano group.

The compound (6) is prepared by reacting the compound (21) with a dehydrating agent (e.g. thionyl chloride, phosphorus pentachloride, phosphorus oxychloride, polyphosphoric acid, etc.) in a solvent, such as ethers (e.g. tetrahydrofuran, dioxane, etc.), aromatic hydrocarbons (e.g. benzene, toluene, etc.), halogenated hydrocarbons (e.g. dichloromethane, chloroform, 1,2-dichloroethane, etc.). Said compound (21) is prepared by reacting a reactive derivative at the carboxyl group of the compound (4) with ammonia by a conventional method.

The compound (3) can also be prepared by a process as shown in the following reaction scheme.

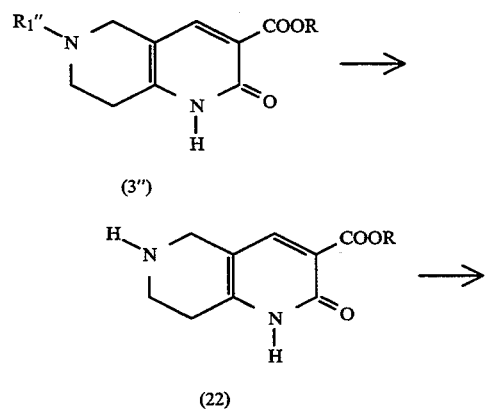

-continued

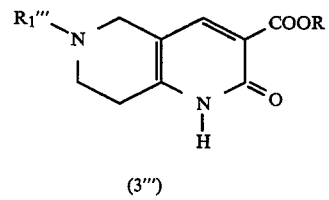

wherein $R_1''$ is a lower alkyl group, benzyl group, a lower alkoxycarbonyl group or benzyloxycarbonyl group, $R_1'''$ is the groups other than hydrogen atom and an acyl group defined for $R_1$, and R is the same as defined above.

The substituent $R_1''$ in the compound (3") and the substituent $R_1'''$ in the compound (3''') can be converted each other via the compound (22). The compound (3") wherein $R_1''$ is a lower alkyl group or benzyl group is converted into the compound (22) by treating it with 1-chloroethyl chlorocarboxylate, etc., according to the method disclosed in Journal of Organic Chemistry, Vol. 49, p. 2081 (1984).

The compound (3") wherein $R_1''$ is benzyl group or benzyloxycarbonyl group is converted into the compound (22) by treating it with hydrogen in the presence of a catalyst (e.g. Raney nickel, palladium-carbon, etc.), under atmospheric pressure or under pressure at a temperature from 25° C. to 80° C. in a suitable solvent, such as water, methanol, ethanol, acetic acid, dioxane, ethyl acetate, and the like.

The compound (3") wherein $R_1''$ is a lower alkoxycarbonyl group or benzyloxycarbonyl group is also converted into the compound (22) by treating it with an acid or a base in a suitable solvent. For example, the compound (3") wherein $R_1''$ is tertbutoxycarbonyl group is treated with trifluoroacetic acid at a temperature from 25° C. to 80° C. in a solvent such as dichloromethane, chloroform, etc., to give the compound (22).

The thus obtained compound (22) is then converted into the compound (3''') by reacting the compound (22) with an alkylating agent corresponding to $R_1'''$ wherein $R_1'''$ is, for example, a lower alkyl, allyl, propargyl, benzyl, naphthalenemethyl, or heteroaromatic methyl group in the presence of a basic compound, such as inorganic salts. For example, alkali metal hydroxides (e.g. sodium hydroxide, potassium hydroxide, etc.), alkali metal carbonates (e.g. sodium carbonate, potassium carbonate, etc.) and alkali metal hydrogen carbonates (e.g. sodium hydrogen carbonate, potassium hydrogen carbonate, etc.), or organic bases, for example, pyridine, triethylamine, tributylamine, etc., in a suitable solvent such as acetone, methyl ethyl ketone, diethyl ketone, dimethylformamide, benzene, toluene, acetonitrile, and the like, at a temperature from 25° C. to 100° C. These alkylating agents may be any conventional ones; such as alkyl halides.

The pharmacological properties of the compounds (I) of the present invention are illustrated by the following experiments with the representative compounds.

Experiment 1 Benzodiazepine Receptor Binding Assay

According to the method disclosed in Life Science Vol. 20, p. 2101 (1977), the benzodiazepine receptor binding assay was carried out.

A crude synaptosome membrane fraction prepared from brains of Wistar rats (age: 7 to 8 weeks) was suspended in 15 mM Tris-HCl buffer (pH 7.4) containing 118 mM sodium chloride, 4.8 mM potassium chloride, 1.28 mM calcium chloride and 1.2 mM magnesium sulfate in a concentration of 1 g (wet weight) of brain per 20 ml of buffer to give a receptor membrane source. [$^3$H]-diazepam was used as a labelled ligand.

A test compound (a known amount), [$^3$H]-diazepam (final concentration; 1.5 nM), receptor membrane and the above buffer were added to a test tube (final volume: 1 ml). The reaction was started by addition of the receptor membrane. The test tube was incubated at 0° C. for 20 minutes, and the reaction mixture was terminated by rapid filtration through Whatman GF/B glass fiber filter attached to a Cell-harvester (manufactured by Brandell). Immediately, the collected labelled ligand-bound receptor membrane was washed three times with ice-cold 50 mM Tris-HCl buffer (pH 7.7, each 5 ml). The radioactivity on the filter was measured by a liquid scintillation counter to determine the amount of the [$^3$H]-diazepam bound to the receptor membrane (total binding). Separately, the same procedures were repeated except 1 µM diazepam was added, and thereby amount of [$^3$H]-diazepam bound to the receptor membrane (non-specific binding) was measured likewise. This non-specific binding was deducted from the total binding to give the specific binding. Based on the specific binding thus obtained, the inhibitory activity (IC$_{50}$) of the test compound was determined by probit method. The IC$_{50}$ means the concentration of the test compound to be required to decrease the specific binding of the labelled ligand by 50%. The results are shown in the following Table 1.

TABLE 1

| Benzodiazepine receptor binding assay | | | |
|---|---|---|---|
| Ex. No. | IC$_{50}$ (nM) | Ex. No. | IC$_{50}$ (nM) |
| 6 | 9.91 | 7 | 13.5 |
| 10 | 6.95 | 26 | 14.1 |
| 29 | 5.46 | 32 | 2.49 |
| 38 | 4.55 | 52 | 19.3 |
| 55 | 3.91 | 56 | 35.1 |
| 58 | 14.6 | 60 | 1.58 |
| 61 | 6.25 | 62 | 13.8 |
| 64 | 4.09 | 66 | 10.1 |
| 81 | 5.17 | 82 | 8.98 |
| 86 | 7.91 | 88 | 4.62 |
| 91 | 23.1 | 115 | 50.3 |
| 119 | 1.29 | 120 | 4.40 |
| 121 | 62.4 | 122 | 5.96 |
| 123 | 12.5 | 124 | 5.40 |
| 125 | 8.63 | 141 | 22.8 |

TABLE 1-continued

| Benzodiazepine receptor binding assay | | | |
|---|---|---|---|
| Ex. No. | IC$_{50}$ (nM) | Ex. No. | IC$_{50}$ (nM) |
| 142 | 3.24 | 143 | 2.19 |
| 145 | 8.64 | 146 | 9.11 |
| 147 | 2.50 | 152 | 4.90 |
| 153 | 3.51 | 154 | 11.0 |
| 155 | 6.08 | 156 | 6.68 |
| 157 | 2.71 | 158 | 3.73 |
| 159 | 8.15 | 160 | 3.75 |

Experiment 2 Activity on pentylenetetrazole-induced clonic convulsion (anti-PTZ activity)

The activity on pentylenetetrazole-induced clonic convulsion of the test compound was tested according to the method of E. A. Swinyard (cf. Anticonvulsant Drugs. Mercier, J., Ed., pp. 47–65, Pergamon Press, New York (1973)). In this test, petit real-type antiepileptics and most of benzodiazepine drugs show positive results.

A test compound was administered orally to Std-ddY male mice (weight; 20–25 g, five mice/group). Two hours later, pentylenetetrazole (85 mg/kg) was injected subcutaneously to the mice, and immediately, the mice were put into a plastic cage, and the appearance of clonic convulsion was observed for 30 minutes. When no clonic convulsion was observed, it was determined that the test compound had antagonistic activity. The results are shown in the following Table 2.

TABLE 2

| | Anti-PTZ activity | | | |
|---|---|---|---|---|
| Ex. No. | Dose of test compd. (mg/kg) | Number of mice having antagonistic activity/ number of test mice | Ex. No. | Dose of test compd. (mg/kg) | Number of mice having antagonistic activity/ number of test mice |
| 6 | 50 | 5/5 | 7 | 50 | 5/5 |
| 10 | 20 | 5/5 | 13 | 20 | 5/5 |
| 17 | 20 | 3/5 | 23 | 10 | 4/5 |
| 26 | 2 | 3/5 | 33 | 10 | 4/5 |
| 35 | 2 | 5/5 | 36 | 2 | 5/5 |
| 38 | 2 | 4/5 | 52 | 10 | 5/5 |
| 55 | 50 | 5/5 | 56 | 50 | 4/5 |
| 60 | 50 | 5/5 | 66 | 50 | 5/5 |
| 80 | 50 | 4/5 | 83 | 50 | 5/5 |
| 85 | 50 | 4/5 | 89 | 50 | 5/5 |
| 91 | 50 | 5/5 | 111 | 50 | 5/5 |
| 119 | 10 | 5/5 | 120 | 10 | 9/10 |
| 122 | 10 | 10/10 | 124 | 10 | 3/5 |
| 142 | 10 | 4/5 | 143 | 10 | 3/5 |

As is shown in the above results, the compounds of the present invention showed the apparent affinity for benzodiazepine receptor, and also showed excellent antagonistic activity against pentylenetetrazole-induced clonic convulsion. Accordingly, the compounds of the present invention are useful as a benzodiazepine receptor agonist, for example, as anxiolytics, antiepileptics, or hypnotics Pharmaceutical use of the compounds of the present invention The compounds of the present invention may be administered either orally, parenterally or intrarectally when used as benzodiazepine receptor agonist, but oral administration is preferable. The dosage of the present compound varies according to the route of the administration, conditions, and ages of the patients, or the types of the treatment (e.g. prophylaxis or treatment) and the like, but it is usually in the range of 0.01 to 10 mg/kg/day, preferably in the range of 0.02 to 5 mg/kg/day.

The present compounds are administered in the form of a conventional pharmaceutical preparation in admixture with a conventional pharmaceutically acceptable carrier or diluent. The pharmaceutically acceptable carrier or diluent may be any conventional one which is used in this field and does not react with the present compound, for example, lactose, glucose, mannitol, dextran, starch, white sugar, magnesium aluminate metasilicate, synthetic aluminum silicate, crystalline cellulose, sodium carboxymethylcellulose, calcium carboxymethylcellulose, ion-exchange resin, methyl cellulose, gelatin, gum arabic, hydroxypropyl cellulose, lower-substituted hydroxypropyl cellulose, hydroxypropylmethyl cellulose, polyvinylpyrrolidone, polyvinyl alcohol, light silicic anhydride, magnesium stearate, talc, carboxyvinyl polymer, titanium oxide, sorbitan fatty acid ester, sodium laurylsulfate, glycerin, glycerin fatty acid ester, purified lanolin, glycerogelatin, polysorbate, macrogol, vegetable oil, wax, liquid paraffin, white petrolatum, nonionic surfactant, propylene glycol, water, and the like.

The pharmaceutical preparations are tablets, capsules, granules, powders, syrups, suspensions, suppositories, gels, injection preparations, and the like. These preparations are prepared by a conventional method. When a liquid preparation is prepared, it may previously be in the form of a solid preparation which is dissolved or suspended in water or a solvent when used. Besides, tablets or granules may be coated by a conventional method, and injection preparations is prepared by dissolving the compound of the present invention or an acid addition salt thereof in distilled water for injection, or a physiological saline solution, but if necessary, it may be dissolved in a isotonic solution, and further, a pH adjustor, a buffer or a preservative may be added thereto.

These pharmaceutical preparations may contain the present compound in an amount of more than 0.01% by weight, preferably 0.05 to 70% by weight, and may contain other pharmacologically active ingredients.

EXAMPLES

The present invention is illustrated in more detail by the following Examples and Reference Examples, but should not be construed to be limited thereto.

Example 1

Preparation of ethyl 6-benzyl-5,6,7,8-tetrahydro-2(1H)-oxo-1,6-naphthyridine-3-carboxylate:

(1) A solution of 1-benzyl-4-piperidone (19 g, 0.1 mole) and pyrrolidine (10.7 g, 0.15 mole) in toluene (200 ml) is refluxed for 5 hours during which water is removed by evaporation. The reaction solution is concentrated to dryness under reduced pressure, and anhydrous toluene (200 ml) is added to the residue. To the mixture is added dropwise and gradually a solution of ethyl ethoxymethylenecyanoacetate (17 g, 0.1 mole) in anhydrous toluene (50 ml) under ice-cooling. The mixture is warmed to room temperature, and stirred overnight, and thereto is added dropwise conc. hydrochloric acid (13 ml) under ice-cooling. The hydrochloride thus obtained is collected by filtration, and washed successively with ethyl acetate and isopropyl ether. The hydrochloride is dissolved in ethanol (300 ml), and thereto is blown ammonia gas under ice-cooling to saturate. The mixture is warmed to room temperature, and allowed to stand overnight, and then, concentrated to dryness under reduced pressure. To the residue is added isopropanol, and the precipitated crystals are collected by filtration, and dried to give the crude crystals (10 g).

The above mentioned crystals are dissolved in ethanol (100 ml), and thereto is added dropwise 10% aqueous sodium hydroxide solution under ice-cooling. The mixture is warmed to room temperature, and stirred for 30 minutes, and thereto is added water (100 ml) under ice-cooling. The precipitated crystals are collected by filtration, and washed with water, and recrystallized from isopropanol to give ethyl 2-amino-6-benzyl-5,6,7,8-tetrahydro-1,6-naphthyridine-3-carboxylate (8.5 g) as a colorless solid.

Yield: 27.3% mp. 141°–143° C.

(2) To a solution of the above ester compound (10 g, 32 mmole) in 10% aqueous sulfuric acid solution (100 ml) is added dropwise and gradually a solution of sodium nitrite (4.5 g, 65 mmole) in water (20 ml) under ice-cooling. After addition, the mixture is stirred for 2 hours. The mixture is alkalified with 20% aqueous sodium hydroxide solution with stirring under ice-cooling, and extracted with chloroform. The extract is dried over anhydrous magnesium sulfate, and evaporated under reduced pressure to remove the solvent. The resulting crystals are recrystallized from isopropanol to give a colorless solid (6.8 g).

Yield: 68% mp. 168°–170° C.

Example 2

Preparation of 6-benzyl-5,6,7,8-tetrahydro-2(1H)-oxo-1,6-naphthyridine-3-carboxylic acid hydrochloride:

(1) A mixture of ethyl 6-benzyl-5,6,7,8-tetrahydro-2(1H)-oxo-1,6-naphthyridine-3-carboxylate (6.8 g, 22 mmole) and 20% aqueous hydrochloric acid solution (70 ml) is refluxed for 3 hours. After cooling, the precipitated crystals are collected by filtration, washed with water, and recrystallized from methanol-water to give the desired compound (7.0 g) as a colorless solid.

Yield: 99.2% m.p. 260°–263° C.

(2) A solution of 1-benzyl-4-piperidone (100 g, 0.53 mole) and pyrrolidine (70 ml, 0.795 mole) in toluene (1.5 liter) is refluxed for 5 hours with distilling off water. The mixture is concentrated to dryness under reduced pressure, and to the residue is added dioxane (1 liter). To the mixture is added diethyl ethoxymethylenemalonate (126 g, 0.58 mole) under ice-cooling, and the mixture is refluxed for 6 hours. The mixture is cooled to room temperature, and thereto is added ammonium acetate (82 g, 1.06 mole), and the mixture is refluxed with stirring for one hour. The reaction solution is concentrated to dryness under reduced pressure to give ethyl 6-benzyl-5,6,7,8-tetrahydro-2(1H)-oxo-1,6-naphthyridine-3-carboxylate, which is used in the subsequent step without isolation or further purification.

To the above ethyl ester is added 20% aqueous hydrochloric acid solution (600 ml), and the mixture is refluxed for 3 hours. After cooling, the precipitated crystals are collected by filtration, washed with water, and recrystallized from methanol-water to give the desired compound as a colorless solid (105 g).

Yield: 61.9% m.p. 260°–263° C.

Example 3

Preparation of ethyl 5,6,7,8-tetrahydro-2(1H)-oxo-1,6-naphthyridine-3-carboxylate acetate:

To a solution of ethyl 6-benzyl-5,6,7,8-tetrahydro-2(1H)-oxo-1,6-naphthyridine-3-carboxylate (8 g) in glacial acetic acid (360 ml) is added 10% palladium-carbon catalyst (200 mg), and the mixture is subjected to catalytic hydrogenation at room temperature under hydrogen gas. After the theoretical amount of hydrogen gas is consumed, the catalyst is removed by filtration. The filtrate is concentrated to dryness under reduced pressure. To the residue is added ethanol, and the precipitated crystal is collected by filtration, and recrystallized from ethanol-water to give a colorless solid (6.8 g).

Yield: 94% m.p. 125°–130° C.

Example 4

Ethyl 6-(3-fluorobenzyl)-5,6,7,8-tetrahydro-2(1H)-oxo-1,6-naphthyridine-3-carboxylate:

A suspension of ethyl 5,6,7,8-tetrahydro-2(1H)-oxo-1,6-naphthyridine-3-carboxylate acetate (2.0 g, 7.1 mmole), 3-fluorobenzyl bromide (1.7 g, 9 mmole) and sodium hydrogen carbonate (2.0 g, 24 mmole) in methyl ethyl ketone (100 ml) is refluxed for 16 hours. The insoluble materials are removed by filtration, and the filtrate is concentrated to dryness under reduced pressure. The residue is purified by medium-pressure column chromatography packed with Diaion CHP-20P (high porous polystyrene resin, manufactured by Mitsubishi Kasei Corporation, Japan) (solvent; acetonitrile and water, with concentration gradient), and recrystallized from ethanol to give a colorless solid (1.91 g).

Yield: 81.4% m.p. 276°–280° C.

Example 5

Preparation of 6-(2-fluorobenzyl)-5,6,7,8-tetrahydro-2(1H)-oxo-1,6-naphthyridine-3-carboxylic acid hydrochloride:

(1) To phenylphosphonic dichloride (1 ml) is added ethyl 6-benzyl-5,6,7,8-tetrahydro-2(1H)-oxo-1,6-naphthyridine-3-carboxylate (1.0 g, 3.2 mmole) at room temperature, and the mixture is stirred at 150° C. for one hour. After cooling, to the mixture is added diisopropyl ether, and the precipitated crystals are collected by filtration. The crystals are suspended in chloroform, and the mixture is alkalified by adding thereto gradually 28% aqueous ammonia with stirring under ice-cooling. The organic layer is separated, dried over anhydrous magnesium sulfate, and evaporated under reduced pressure to remove the solvent. The resulting oily product is purified by silica gel column chromatography (solvent; chloroform:methanol=200:1) to give ethyl 6-benzyl-2-chloro-5,6,7,8-tetrahydro-1,6-naphthyridine-3-carboxylate (0.7 g) as a colorless oil.

Yield: 66.1%

(2) To a solution of the above ester (20.0 g, 60 mmole) in methylene chloride (200 ml) is added dropwise 1-chloroethyl chloroformate (10.4 g, 72 mmole) at room temperature, and the mixture is refluxed for 20 hours. The mixture is concentrated to dryness under reduced pressure, and to the resulting residue is added methanol (200 ml). The mixture is heated with stirring at 40° C. for 2 hours. The reaction mixture is concentrated to dryness under reduced pressure, and isopropyl ether is added to the residue. The precipitated crystals are collected by filtration, and recrystallized from ethanol to give ethyl 2-chloro-5,6,7,8-tetrahydro-1,6-naphthyridine-3-carboxylate hydrochloride (21.2 g) as a colorless solid.

Yield: 85.8% m.p. 153°–156° C.

(3) To a solution of the above hydrochloride (5.0 g, 18 mmole) and triethylamine (4.0 g, 40 mmole) in N,N-dimethylformamide (DMF) (50 ml) is added 2-fluorobenzyl bromide (3.1 g, 21 mmole), and the mixture is heated with stirring at 60° C. for 15 hours. The reaction solution is concentrated to dryness under reduced pressure, and the residue is dissolved in chloroform. The mixture is washed successively with 10% aqueous potassium carbonate solution and water. The organic layer is dried over anhydrous magnesium sulfate, and evaporated under reduced pressure to remove the solvent. The resulting oily product is purified by silica gel column chromatography (solvent; chloroform:methanol=100:1) to give ethyl 2-chloro-6-(2-fluorobenzyl)-5,6,7,8-tetrahydro-1,6-naphthyridine-3-carboxylate (4.6 g) as a colorless oil.

Yield: 73.3%

(4) A solution of the above ester (4.6 g, 13 mmole) in 20% aqueous hydrochloric acid solution (80 ml) is refluxed for 24 hours. After cooling, the precipitated crystals are collected by filtration, washed, and recrystallized from ethanol to give the desired compound (3.4 g) as a colorless solid.

Yield: 77.2% m.p. 273°–276° C.

Example 6

Preparation of 6-benzyl-3-(5-methoxy-1,3,4-oxadiazol-2-yl)-5,6,7,8-tetrahydro-1,6-naphthyridine-2(1H)-one:

(1) A solution of 6-benzyl-5,6,7,8-tetrahydro-2(1H)-oxo-1,6-naphthyridine-3-carboxylic acid hydrochloride (3.0 g, 9.4 mmole) and N,N'-carbonyldiimidazole (2.3 g, 14 mmole) in DMF (50 ml) is heated with stirring at 70° C. for 3 hours. To the solution is added methyl carbazate (1.0 g, 11 mmole), and the mixture is stirred at the same temperature for 2 hours. The reaction solution is concentrated to dryness under reduced pressure, and to the residue are added isopropanol and triethylamine. The precipitated crystals are collected by filtration, and recrystallized from methanol to give N'-methoxycarbonyl-6-benzyl-5,6,7,8-tetrahydro-2(1H)-oxo-1,6-naphthyridine-3-carbohydrazide (2.4 g) as a colorless solid.

Yield: 71.6% m.p. 240°–242° C.

(2) To a solution of the above product (2.0 g, 5.6 mmole), triphenylphosphine (3.0 g, 11 mmole) and triethylamine (2.0 g, 20 mmole) in anhydrous tetrahydrofuran (THF) (50 ml) is added dropwise with stirring a solution of diisopropyl azodicarboxylate (2.2 g, 11 mmole) in anhydrous tetrahydrofuran (10 ml) under ice cooling.

The mixture is stirred at room temperature for one hour, and thereto is added a small amount of water, and the mixture is concentrated to dryness under reduced pressure. To the residue is added isopropanol, and the precipitated crystals are collected by filtration, and recrystallized from acetonitrile to give the desired compound (0.8 g) as a colorless solid.

Yield: 43% m.p. 176°–178° C.

Examples 7–54

In the same manner as described in Example 6, there are prepared the compounds of Examples 7–54 as listed in Table 3.

TABLE 3

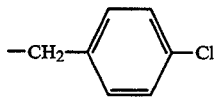

| Ex. No. | R₁ | R₂ | m.p. (°C.) | Solvent for recrystal. |
|---|---|---|---|---|
| 7 | —CH₂—C₆H₄—Cl (4-Cl) | —OCH₃ | 182–184 | Ethanol |
| 8 | —CH₂—C₆H₄—Me (4-Me) | —OCH₃ | 183–185 | Ethanol |
| 9 | —CH₂—C₆H₄—Me (3-Me) | —OCH₃ | 187–189 | Ethanol |
| 10 | —CH₂—C₆H₄—Cl (2-Cl) | —OCH₃ | 189–191 | Ethanol |
| 11 | —CH₂—C₆H₄—OMe (4-OMe) | —OCH₃ | 183–185 | Ethanol |
| 12 | —CH₂—C₆H₄—Me (2-Me) | —OCH₃ | 179–181 | Ethanol |
| 13 | —CH₂—C₆H₄—F (3-F) | —OCH₃ | 184–186 | Ethanol |
| 14 | —CH₂—C₆H₄—F (4-F) | —OCH₃ | 203–205 | Ethanol |
| 15 | —CH₂—C₆H₄—Cl (3-Cl) | —OCH₃ | 184–185 | Ethanol |

TABLE 3-continued

[Structure: R₁-N (tetrahydro-naphthyridinone core with N-H and C=O) connected to C(=N-N=C(R₂))-O (1,3,4-oxadiazole ring)]

| Ex. No. | R₁ | R₂ | m.p. (°C.) | Solvent for recrystal. |
|---------|-----|-----|------------|------------------------|
| 16 | —CH₂—(3-CF₃-phenyl) | —OCH₃ | 192–194 | Methanol |
| 17 | —CH₂—(3-OMe-phenyl) | —OCH₃ | 178–180 | Ethanol |
| 18 | —CH₂—(1-naphthyl) | —OCH₃ | 178–180 | Ethanol |
| 19 | —CH₂—(2-pyridyl) | —OCH₃ | 171–173 | Acetonitrile |
| 20 | —CH₂—(3-pyridyl) | —OCH₃ | 167–169 | Acetonitrile |
| 21 | —CH₂—(3-Br-phenyl) | —OCH₃ | 185–187 | Ethanol |
| 22 | —CH₂—(2-F-phenyl) | —OCH₃ | 174–176 | Ethanol |
| 23 | —CH₂—(3-NO₂-phenyl) | —OCH₃ | 185–187 | Ethanol |
| 24 | —CH₂—(2,5-diF-phenyl) | —OCH₃ | 206–208 | Ethanol |

TABLE 3-continued

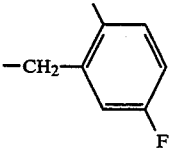

| Ex. No. | R₁ | R₂ | m.p. (°C.) | Solvent for recrystal. |
|---|---|---|---|---|
| 25 | 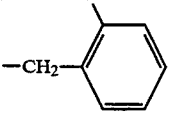 -CH₂-(2,5-difluorophenyl) | —OCH₃ | 202–204 | Ethanol |
| 26 | 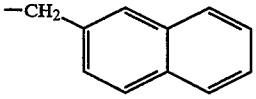 -CH₂-(2-bromophenyl) | —OCH₃ | 191–193 | Ethanol |
| 27 | -CH₂-(naphthalen-2-yl) | —OCH₃ | 203–205 | Methanol |
| 28 | 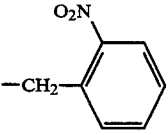 -CH₂-(2-nitrophenyl) | —OCH₃ | 194–196 | Methanol |
| 29 | 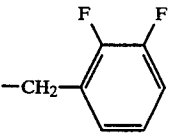 -CH₂-(2,3-difluorophenyl) | —OCH₃ | 195–197 | Ethanol |
| 30 | 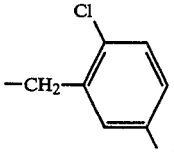 -CH₂-(2,5-dichlorophenyl) | —OCH₃ | 193–195 | Methanol |
| 31 | 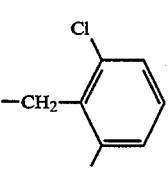 -CH₂-(2,3-dichlorophenyl) | —OCH₃ | 199–201 | Methanol |
| 32 | 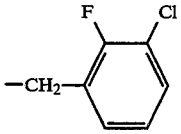 -CH₂-(2-fluoro-3-chlorophenyl) | —OCH₃ | 177–179 | Ethanol |
| 33 | 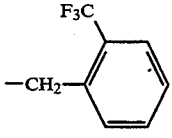 -CH₂-(2-trifluoromethylphenyl) | —OCH₃ | 189–191 | Methanol |

TABLE 3-continued
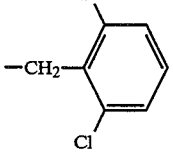
| Ex. No. | R$_1$ | R$_2$ | m.p. (°C.) | Solvent for recrystal. |
|---|---|---|---|---|
| 34 | —CH$_2$—(2-F,6-Cl-C$_6$H$_3$) | —OCH$_3$ | 187–189 | Ethanol |
| 35 | —CH$_2$—(2,6-F$_2$-C$_6$H$_3$) | —OCH$_3$ | 186–188 | Ethanol |
| 36 | —CH$_2$—(2,3,6-F$_3$-C$_6$H$_2$) | —OCH$_3$ | 199–201 | Ethanol |
| 37 | —CH$_2$—C$_6$F$_5$ | —OCH$_3$ | 210–212 | Methanol |
| 38 | —CH$_2$—(2-Br,5-F-C$_6$H$_3$) | —OCH$_3$ | 208–210 | Methanol |
| 39 | —CH$_2$—(4-OCF$_3$-C$_6$H$_4$) | —OCH$_3$ | 213–215 | Ethanol |
| 40 | —CH$_2$—(3-I-C$_6$H$_4$) | —OCH$_3$ | 185–187 | Ethanol |
| 41 | —CH$_2$—(2,5-Br$_2$-C$_6$H$_3$) | —OCH$_3$ | 219–221 | Methanol |

TABLE 3-continued
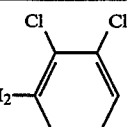
| Ex. No. | R₁ | R₂ | m.p. (°C.) | Solvent for recrystal. |
|---|---|---|---|---|
| 42 | 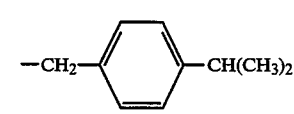 —CH₂— (2,3-diCl-phenyl) | —OCH₃ | 193–195 | Methanol |
| 43 | —CH₂— (4-isopropyl-phenyl) | —OCH₃ | 195–197 | Acetonitrile |
| 44 | —CH₂— (4-Br-phenyl) | —OCH₃ | 191–193 | Ethanol |
| 45 | —CH₂— (2-Cl-4-F-phenyl) | —OCH₃ | 194–196 | Ethanol |
| 46 | —CH₂— (2-F-4-Cl-phenyl) | —OCH₃ | 190–192 | Ethanol |
| 47 | —CH₂— (4-CF₃-phenyl) | —OCH₃ | 207–209 | Ethanol |
| 48 | —CH₂— (2,5-diCH₃-phenyl) | —OCH₃ | 181–183 | Ethanol |
| 49 | —CH₂— (4-C₂H₅-phenyl) | —OCH₃ | 181–183 | Acetonitrile |
| 50 | —CH₂— (2-thienyl) | —OCH₃ | 153–155 | Acetonitrile |
| 51 | —CH₂— (2,4-diF-phenyl) | —OCH₃ | 196–198 | Ethanol |

TABLE 3-continued

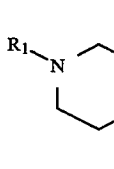

| Ex. No. | R₁ | R₂ | m.p. (°C.) | Solvent for recrystal. |
|---|---|---|---|---|
| 52 | 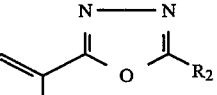 | —OCH₃ | 209–211 | Ethanol |
| 53 | 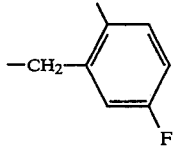 | —OCH₃ | 156–158 | Acetonitrile |
| 54 | 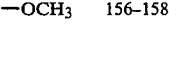 | —OCH₃ | 187–189 | Ethanol |

Example 55

Preparation of 6-benzyl-3-(5-cyclopropyl-1,3,4-oxadiazol-2-yl)-5,6,7,8-tetrahydro-1,6-naphthyridin-2(1H)-one:

(1) A solution of 6-benzyl-5,6,7,8-tetrahydro-2(1H)-oxo-1,6-naphthyridine-3-carboxylic acid hydrochloride (1.5 g, 4.7 mmole) and N,N'-carbonyldiimidazole (1.14 g, 7 mmole) in DMF (30 ml) is, heated with stirring at 70° C. for 3 hours. To the solution is added cyclopropanecarbohydrazide (0.51 g, 5.2 mmole), and the mixture is stirred at the same temperature for 2 hours. The reaction solution is concentrated to dryness under reduced pressure, and to the residue are added isopropanol and triethylamine. The precipitated crystals are collected by filtration, and recrystallized from methanol to give N'-cyclopropanecarbonyl 6-benzyl-5,6,7,8-tetrahydro-2(1H)-oxo-1,6-naphthyridine-3-carbohydrate (1.2 g) as a colorless solid.

Yield: 66.1% m.p. 256°–258° C.

(2) To a solution of the above product (1.1 g, 2.9 mmole), triphenylphosphine (1.62 g, 6.2 mmole) and triethylamine (1.05 g, 10 mmole) in anhydrous THF (75 ml) is added dropwise with stirring a solution of diethyl azodicarboxylate (1.05 g, 6 mmole) in anhydrous THF (5 ml) under ice-cooling. The mixture is heated with stirring at 60° C. for 2 hours, and thereto is added a small amount of water, and concentrated to dryness. The residue is purified by medium-pressure column chromatography of Diaion CHP-20P (solvent; acetonitrile and water, with concentration gradient), and recrystallized from acetonitrile to give a colorless solid (0.31 g).

Yield: 44.5% m.p. 212°–214° C.

Examples 56–110

In the same manner as described in Example 55, there are prepared the compounds listed in Table 4.

TABLE 4

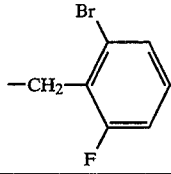

| Ex. No. | R₁ | R₂ | m.p. (°C.) | Solvent for recrystal. |
|---|---|---|---|---|
| 56 | 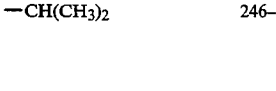 | —CH(CH₃)₂ | 246–250 | Methanol |

TABLE 4-continued
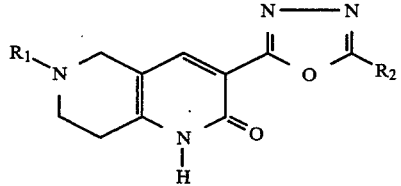
| Ex. No. | R₁ | R₂ | m.p. (°C.) | Solvent for recrystal. |
|---|---|---|---|---|
| 57 | —CH₂—C₆H₅ | —OC₂H₅ | 211–213 | Ethanol |
| 58 | —CH₂—C₆H₅ | —C₆H₅ | 258–260 | Methanol |
| 59 | —CH₂—C₆H₅ | 2-pyridyl | 252–255 | Methanol |
| 60 | —CH₂—C₆H₅ | 2-thienyl | 239–242 | Ethanol |
| 61 | —CH₂—C₆H₅ | 2-Cl-C₆H₄— | 227–230 | Methanol |
| 62 | —CH₂—C₆H₅ | —(CH₂)₂CH₃ | 219–221 | Ethanol |
| 63 | —CH₂—C₆H₅ | 4-CH₃O-C₆H₄— | 221–224 | Methanol |
| 64 | —CH₂—C₆H₅ | 2-furyl | 224–227 | Ethanol |
| 65 | —CH₂—C₆H₅ | 2-F-C₆H₄— | 229–231 | Methanol |
| 66 | —CH₂—C₆H₅ | 3,5-dimethylisoxazol-4-yl | 247–250 | Methanol |
| 67 | —CH₂—C₆H₅ | 4-NO₂-C₆H₄— | 224–226 | THF |

TABLE 4-continued
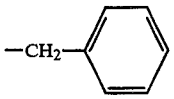
| Ex. No. | R₁ | R₂ | m.p. (°C.) | Solvent for recrystal. |
|---|---|---|---|---|
| 68 | —CH₂— | 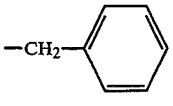 | 207–209 | Acetonitrile |
| 69 | —CH₂—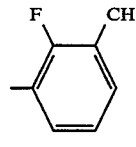 | 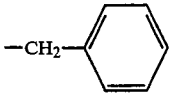 | 232–234 | THF |
| 70 | —CH₂—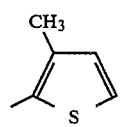 | 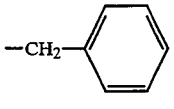 | 234–236 | Methanol |
| 71 | —CH₂—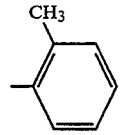 | 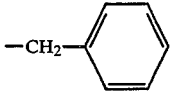 | 231–233 | Methanol |
| 72 | —CH₂—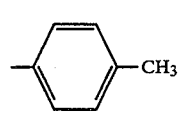 | 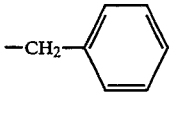 | 239–241 | Methanol |
| 73 | —CH₂—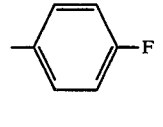 | 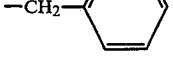 | 230–232 | Methanol |
| 74 | —CH₂—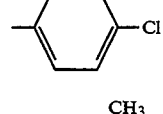 | 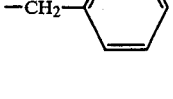 | 241–243 | THF |
| 75 | —CH₂—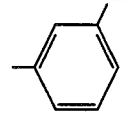 | 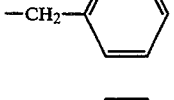 | 258–260 | Chloroform |
| 76 | —CH₂—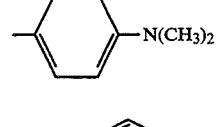 | 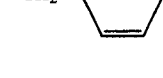 | 224–226 | Methanol |
| 77 | —CH₂—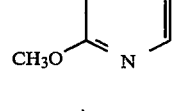 | 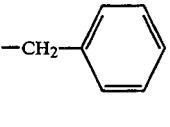 | 216–218 | Methanol |
| 78 | —CH₂—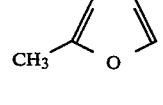 | (CH₃, O furan) | 259–261 | Methanol |

TABLE 4-continued
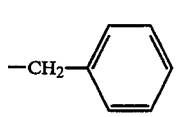
| Ex. No. | R₁ | R₂ | m.p. (°C.) | Solvent for recrystal. |
|---|---|---|---|---|
| 79 | —CH₂—C₆H₅ | 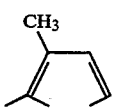 | 228–230 | Methanol |
| 80 | —CH₂—C₆H₄—CH₃ (p) | 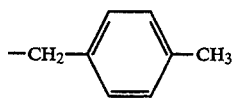 | 214–216 | Acetonitrile |
| 81 | —CH₂—C₆H₄—CH₃ (o) |  | 224–226 | Ethanol |
| 82 | —CH₂—C₆H₄—Cl (p) | 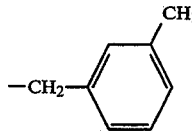 | 222–224 | Acetonitrile |
| 83 | —CH₂—C₆H₄—Cl (o) |  | 221–223 | Acetonitrile |
| 84 | —CH₂—C₆H₅ | —CH₃ | 226–228 | Ethanol |
| 85 | —CH₂—C₆H₄—OCH₃ (p) | 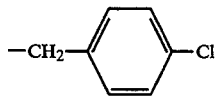 | 184–186 | Acetonitrile |
| 86 | —CH₂—C₆H₄—OCH₃ (o) |  | 212–214 | Acetonitrile |
| 87 | —CH₂—C₆H₄—F (p) | 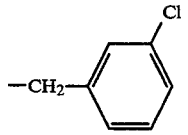 | 212–214 | Acetonitrile |
| 88 | —CH₂—C₆H₄—F (o) |  | 219–221 | Ethanol |

TABLE 4-continued
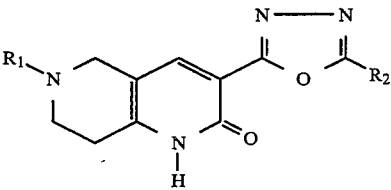
| Ex. No. | R₁ | R₂ | m.p. (°C.) | Solvent for recrystal. |
|---|---|---|---|---|
| 89 | 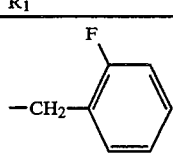 |  | 210–212 | Acetonitrile |
| 90 | 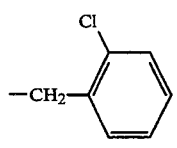 |  | 225–227 | Ethanol |
| 91 | 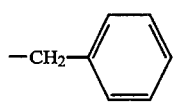 | —C₂H₅ | 213–215 | Ethanol |
| 92 |  | 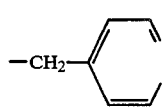 | 230–232 | Acetonitrile |
| 93 |  | 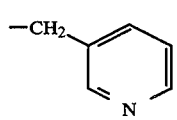 | 209–211 | Acetonitrile |
| 94 | —CH₂CH=CH₂ |  | 205–207 | Acetonitrile |
| 95 |  |  | 214–216 | Acetonitrile |
| 96 | 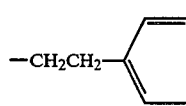 |  | 206–208 | Acetonitrile |
| 97 | 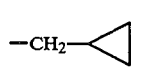 |  | 220–222 | Acetonitrile |
| 98 | 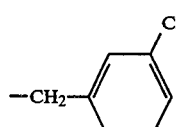 |  | 192–194 | Acetonitrile |
| 99 | 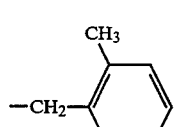 |  | 213–215 | Ethanol |

TABLE 4-continued

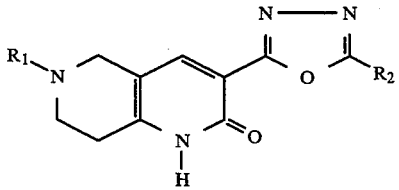

| Ex. No. | R₁ | R₂ | m.p. (°C.) | Solvent for recrystal. |
|---|---|---|---|---|
| 100 | —(CH₂)₂CH₃ |  | 197–199 | Acetonitrile |
| 101 | —CH₂—⟨phenyl⟩ | —CH₂OCH₃ | 187–189 | Acetonitrile |
| 102 | —CH₂—⟨naphthyl⟩ | 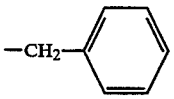 | 218–220 | Acetonitrile |
| 103 | —CH₂—⟨2-methylthiazol-4-yl⟩ | 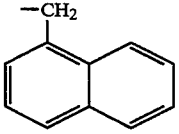 | 197–199 | Acetonitrile |
| 104 | —CH(CH₃)₂ |  | 201–203 | Acetonitrile |
| 105 | —CH₂CH(CH₃)₂ | 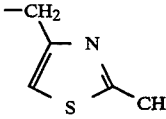 | 223–225 | Acetonitrile |
| 106 | —CH₂—⟨phenyl⟩ | —(CH₂)₃CH₃ | 195–197 | Ethanol |
| 107 | —CH₂—⟨phenyl⟩ | ⟨cyclohexyl⟩ | 253–256 | Methanol |
| 108 | —CH₂—⟨phenyl⟩ | ⟨1-methylcyclopropyl⟩ | 242–244 | Ethanol |
| 109 | —CH₂—⟨phenyl⟩ | ⟨4-CF₃-phenyl⟩ | 254–256 | Chloroform |
| 110 | —CH₂—⟨phenyl⟩ | —CH₂CH₂CF₃ | 224–226 | Ethanol |

Example 111

Preparation of 6-benzyl-3-(5-isopropenyl-1,3,4-oxadazol-2-yl)-5,6,7,8-tetrahydro-1,6-naphthyridin-2(1H)-one:

(1) To a solution of 6-benzyl-5,6,7,8-tetrahydro-2(1H)-oxo-1,6-naphthyridine-3-carbohyrazide (1.49 g, 5 mmole) in pyridine (20 ml) is added with stirring methacryloyl chloride (0.57 g, 5.5 mmole) under ice-cooling. The mixture is warmed to room temperature, and stirred for 2 hours, and concentrated to dryness under reduced pressure. To the residue is added 10% aqueous potassium carbonate solution, and the mixture is extracted with chloroform. The organic layer is dried over anhydrous sodium sulfate, and evaporated under reduced pressure to remove the solvent. To the residue is added isopropanol, and the precipitated crystals are collected by filtration, and recrystallized from methanol to give N'-methacryloyl 6-benzyl-5,6,7,8-tetrahydro-2(1H)-oxo-1,6-naphthyridine-3-carbohyrazide (1.21 g) as a colorless solid.

Yield: 66% m.p. 245°–248° C.

(2) To a solution of the above product (0.92 g, 2.5 mmole), triphenylphosphine (1.35 g, 5 mmole) and triethylamine (0.87 g, 8.6 mmole) in anhydrous THF (50 ml) is added dropwise with stirring a solution of diethyl azodicarboxylate (0.87 g, 5 mmole) in anhydrous THF (5 ml) under ice-cooling. The mixture is heated with stirring at 60° C. for 2 hours, and thereto is added a small amount of water, and concentrated to dryness under reduced pressure. To the residue is added isopropanol, and the precipitated crystals are collected by filtration, and recrystallized from acetonitrile to give a colorless solid (0.39 g).

Yield: 44.8% m.p. 221°–223° C.

Examples 112–116

In the same manner as described in Example 111, there are prepared the compounds listed in Table 5.

TABLE 5

[Structure: naphthyridine with $R_1$-N group, attached oxadiazole with $R_2$ substituent]

| Ex. No. | $R_1$ | $R_2$ | m.p. (°C.) | Solvent for recrystal. |
|---|---|---|---|---|
| 112 | —CH$_2$—(phenyl) | —CH=CHCH$_3$ | 210–212 | Acetonitrile |
| 113 | —CH$_2$—(phenyl) | —OCH(CH$_3$)$_2$ | 209–211 | Ethanol |
| 114 | —CH$_2$—(phenyl) | —(phenyl)—O—(phenyl) | 230–232 | Methanol |
| 115 | —CH$_2$—(phenyl) | —CF$_3$ | 230–232 | Acetonitrile |
| 116 | —CH$_2$—(phenyl) | —OC(=CH$_2$)CH$_3$ | 190–192 | Acetonitrile |

Example 117

Preparation of 6-benzyl-3-(5-methylthio-1,3,4-oxadiazol-2-yl)-5,6,7,8-tetrahydro-1,6-naphthyridin-2(1H)-one:

(1) To a solution of 6-benzyl-5,6,7,8-tetrahydro-2(1H)-oxo-1,6-naphthyridine-3-carbohydrazide (1.49 g, 5 mmole) in ethanol (20 ml) is added a solution of potassium hydroxide (0.29 g) in water (1 ml), and further thereto is added with stirring carbon disulfide (0.46 g, 6 mmole) under ice-cooling, and the mixture is refluxed for 7 hours. After cooling, the precipitated crystals are collected by filtration to give 2-(6-benzyl-5,6,7,8-tetrahydro-2(1H)-oxo-1,6-naphthyridin-3-yl)-1,3,4-oxadiazole-5-thiol potassium salt (1.88 g) as a colorless solid.

Yield: 99%

(2) To a solution of the above product (1.14 g, 3 mmole) in methanol (500 ml) is added methyl iodide (0.51 g, 3.6 mmole), and the mixture is stirred at room temperature for 3 hours. The reaction solution is concentrated to dryness under reduced pressure, and to the residue is added isopropanol. The precipitated crystals are collected by filtration, and recrystallized from ethanol to give the desired compound (0.59 g) as a colorless solid.

Yield: 55.5% m.p. 215°–217° C.

Example 118

Preparation of 6-benzyl-5,6,7,8-tetrahydro-2(1H)-oxo-1,6-naphthyridine-3-carbonitrile:

(1) A solution of 1-benzyl-4-piperidone (26.8 g, 0.14 mole) and pyrrolidine (20 g, 0.28 mole) in toluene (300 ml) is refluxed for 4 hours with distilling off water. The reaction solution is concentrated to dryness under reduced pressure, and to the residue is added anhydrous dioxane (300 ml). To the mixture is added dropwise gradually with stirring a solution of ethoxymethylenemalononitrile (19 g, 0.16 mole) in anhydrous dioxane (40 ml) under ice-cooling. The mixture is warmed to room temperature, and stirred for one hour. To the mixture is added ammonium acetate (22 g, 0.29 mole), and the mixture is stirred at 70° C. overnight, and concentrated to dryness under reduced pressure. To the residue is added isopropanol, and the precipitate crystals are collected by filtration, washed with water, and dried to give 2-amine-6-benzyl-5,6,7,8-tetrahydro-1,6-naphthyridine-3-carbonitrile (18.3 g, yield; 49%), which is used in the subsequent reaction without purification.

(2) To a solution of the above product (15 g, 56.7 mmole) in 10% aqueous sulfuric acid solution (150 ml) is added dropwise with stirring sodium nitrite (7.83 g, 113 mmole) under ice-cooling, and when, the mixture is stirred for 2 hours. The mixture is alkalified by adding 20% aqueous sodium hydroxide solution thereto with stirring under ice-cooling. The mixture is extracted with chloroform, and the extract is dried over anhydrous sodium sulfate, and evaporated under reduced pressure to remove the solvent. To the residue is added isopropanol, and the precipitated crystals are collected by filtration, and recrystallized from acetonitrile to give the desired compound (10 g) as a colorless solid.

Yield: 66% m.p. 230°–233° C.

Example 119

Preparation of 6-benzyl-3-(5-cyclopropyl-1,2,4-oxadiazol-3-yl)-5,6,7,8-tetrahydro-1,6-naphthyridin-2(1H)-one:

(1) To a solution of 6-benzyl-5,6,7,8-tetrahydro-2(1H)-oxo-1,6-naphthyridine-3-carbonitrile (1.6 g, 6 mmole) in ethanol (30 ml) are added hydroxylamine hydrochloride (0.52 g, 7.5 mmole) and sodium carbonate (0.8 g, 7.5 mmole), and the mixture is refluxed with stirring overnight. The reaction solution is concentrated to dryness under reduced pressure, and water is added to the residue. The precipitated crystals are collected by filtration, washed with isopropanol, and dried to give amide oxime (1.4 g) as a colorless solid, which is used in the subsequent reaction without purification.

(2) To a suspension of the above product (1.19 g, 4 mmole) and potassium carbonate (0.66 g, 4.2 mmole) in methyl ethyl ketone (50 ml) is added dropwise with stirring a solution of cyclopropanecarbonyl chloride (0.44 g, 4.2 mmole) in methyl ethyl ketone (3 ml) under ice-cooling. The mixture is warmed to room temperature, and the mixture is stirred for 2 hours. The reaction solution is concentrated to dryness under reduced pressure, and water is added to the residue. The precipitated crystals are collected by filtration, and washed successively with water and isopropanol. A mixture of the crystals thus obtained and toluene (50 ml) is refluxed for 24 hours, and concentrated to dryness under reduced pressure. The residue is purified by silica gel column chromatography (solvent; chloroform:methanol=100:3), and recrystallized from acetonitrile to give the desired compound (0.93 g) as a colorless solid.

Yield: 66.7%
m.p. 187°–190° C.

Examples 120–140

In the same manner as described in Example 119, there are prepared the compounds listed in Table 6.

TABLE 6

| Ex. No. | $R_1$ | $R_2$ | m.p. (°C.) | Solvent for recrystal. |
|---|---|---|---|---|
| 120 | —CH$_2$—C$_6$H$_5$ | —C$_2$H$_5$ | 230–232 | Acetonitrile |
| 121 | —CH$_2$—C$_6$H$_5$ | —C$_6$H$_5$ | 239–241 | Ethanol |
| 122 | —CH$_2$—C$_6$H$_5$ | —CH$_3$ | 232–235 | Ethanol |
| 123 | —CH$_2$—C$_6$H$_5$ | 2-thienyl | 230–233 | Chloroform/Ethanol |
| 124 | —CH$_2$—C$_6$H$_5$ | —CH(CH$_3$)$_2$ | 191–194 | Ethanol |
| 125 | —CH$_2$—C$_6$H$_5$ | —(CH$_2$)$_2$CH$_3$ | 175–177 | Ethanol |

Examples 126–140

Using the suitable starting compounds, the same procedures as Example 119 are repeated to give the compounds listed in Table 7.

TABLE 7

| Ex. No. | $R_1$ | $R_2$ |
|---|---|---|
| 126 | —CH$_2$—C$_6$H$_5$ | —CH$_2$CH=CH$_2$ |
| 127 | —CH$_2$—C$_6$H$_5$ | —C(CH$_3$)=CH$_2$ |
| 128 | —CH$_2$—C$_6$H$_5$ | —CH=CHCH$_3$ |
| 129 | —CH$_2$—C$_6$H$_5$ | 1-methylcyclopropyl |
| 130 | —CH$_2$—(2-Cl-C$_6$H$_4$) | cyclopropyl |
| 131 | —CH$_2$—(3-Cl-C$_6$H$_4$) | cyclopropyl |
| 132 | —CH$_2$—(4-Cl-C$_6$H$_4$) | cyclopropyl |
| 133 | —CH$_2$—(2-Br-C$_6$H$_4$) | cyclopropyl |
| 134 | —CH$_2$—(3-Br-C$_6$H$_4$) | cyclopropyl |
| 135 | —CH$_2$—(2-F-C$_6$H$_4$) | cyclopropyl |

TABLE 7-continued

[Structure: R₁-N substituted 5,6,7,8-tetrahydro-1,6-naphthyridin-2(1H)-one with 1,2,4-oxadiazol-5-yl substituent bearing R₂]

| Ex. No. | R₁ | R₂ |
|---|---|---|
| 136 | —CH₂—(3-F-phenyl) | cyclopropyl |
| 137 | —CH₂—(2-CH₃-phenyl) | cyclopropyl |
| 138 | —CH₂—(3-CH₃-phenyl) | cyclopropyl |
| 139 | —CH₂—(3-OCH₃-phenyl) | cyclopropyl |
| 140 | —CH₂—(3-Br,5-F-phenyl) | cyclopropyl |

Example 141

Preparation of 6-benzyl-3-(3-phenyl-1,2,4-oxadiazol-5-yl)-5,6,7,8-tetrahydro-1,6-naphthyridin-2(1H)-one:

(1) To a suspension of 6-benzyl-5,6,7,8-tetrahydro-2(1H)-oxo-1,6-naphthyridine-3-carboxylic acid hydrochloride (1.6 g, 5 mmole) and triethylamine (0.56 g, 5.5 mmole) in 1,2-dichloroethane (50 ml) is added N,N'-carbonyldiimidazole (1.22 g, 7.5 mmole), and the mixture is heated with stirring at 70° C. for 3 hours. The mixture is cooled to room temperature, and thereto is added benzamide oxime (0.82 g, 6 mmole), and the mixture is stirred for 2 hours The reaction solution is concentrated to dryness under reduced pressure, and to the residue is added isopropanol. The precipitated crystals are collected by filtration to give a colorless solid (1.4 g, yield; 70%), which is used in the subsequent reaction without purification.

(2) A solution of the above product (1.4 g) in toluene (50 ml) is refluxed overnight. The reaction solution is concentrated to dryness under reduced pressure, and the residue is purified by silica gel column chromatography (solvent; chloroform:methanol=100:3), and recrystallized from chloroform/methanol to give the desired compound (0.91 g) as a colorless solid.

Yield: 68% m.p. 231°–233° C.

Examples 142–167

Using the corresponding starting compounds, the same procedures as in Example 141 are repeated to give the compounds listed in Table 8.

TABLE 8

[Structure: R₁-N substituted 5,6,7,8-tetrahydro-1,6-naphthyridin-2(1H)-one with 1,2,4-oxadiazol-3-yl substituent bearing R₂]

| Ex. No. | R₁ | R₂ | m.p. (°C.) | Solvent for recrystal. |
|---|---|---|---|---|
| 142 | —CH₂—phenyl | —C₂H₅ | 232–235 | Methanol |
| 143 | —CH₂—phenyl | cyclopropyl | 198–235 | Ethanol |
| 144 | —CH₂—phenyl | —CH₃ | 231–234 | Methanol |

TABLE 8-continued
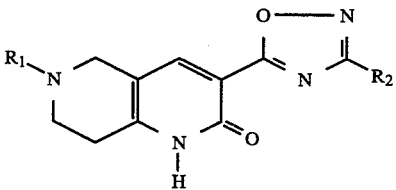
| Ex. No. | R₁ | R₂ | m.p. (°C.) | Solvent for recrystal. |
|---|---|---|---|---|
| 145 | —CH₂—C₆H₅ | 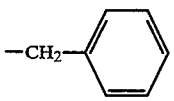 (2-thienyl) | 226–229 | Methanol |
| 146 | —CH₂—C₆H₅ | —CH(CH₃)₂ | 206–208 | Ethanol |
| 147 | —CH₂—C₆H₅ | —(CH₂)₂CH₃ | 185–187 | Ethanol |
| 148 | —CH₂—C₆H₅ | —CH₂CH=CH₂ | | |
| 149 | —CH₂—C₆H₅ | —C(CH₃)=CH₂ | | |
| 150 | —CH₂—C₆H₅ | —CH=CHCH₃ | | |
| 151 | —CH₂—C₆H₅ | 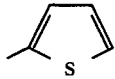 (1-methylcyclopropyl) | | |
| 152 | —CH₂—(2-Cl-C₆H₄) | cyclopropyl | 226–228 | Ethanol |
| 153 | —CH₂—(3-Cl-C₆H₄) | cyclopropyl | 224–226 | Ethanol |
| 154 | —CH₂—(4-Cl-C₆H₄) | cyclopropyl | 239–241 | Ethanol |
| 155 | —CH₂—(2-Br-C₆H₄) | cyclopropyl | 229–231 | Ethanol |

TABLE 8-continued

[Structure: R₁-N (in tetrahydronaphthyridinone ring system) with substituent -C(=N-)- linked to oxadiazole bearing R₂, and 2-oxo-1H group]

| Ex. No. | R₁ | R₂ | m.p. (°C.) | Solvent for recrystal. |
|---|---|---|---|---|
| 156 | —CH₂—(phenyl with Br at ortho) | cyclopropyl | 219–221 | Ethanol |
| 157 | —CH₂—(phenyl with F at ortho) | cyclopropyl | 205–207 | Ethanol |
| 158 | —CH₂—(phenyl with F at meta) | cyclopropyl | 200–202 | Ethanol |
| 159 | —CH₂—(phenyl with CH₃ at ortho) | cyclopropyl | 232–234 | Ethanol |
| 160 | —CH₂—(phenyl with CH₃ at meta) | cyclopropyl | 226–229 | Ethanol |
| 161 | —CH₂—(phenyl with OCH₃ at meta) | cyclopropyl | | Ethanol |
| 162 | —CH₂—(phenyl with Br at ortho, F at para) | cyclopropyl | | |

Example 163

Preparation of 6-benzyl-3-(5-methoxy-1,2,4-oxadiazol-3-yl)-5,6,7,8-tetrahydro-1,6-naphthyridin-2(1H)-one:

(1) To a mixture of O-methoxycarbonyl 6-benzyl-5,6,7,8-tetrahydro-2(1H)-oxo-1,6-naphthyridine-3-azidoxime (3.8 g, 10 mmole) and dichloromethane (40 ml) is added dropwise with stirring a solution of triphenylphosphine (2.7 g, 10 mmole) in dichloromethane (20 ml) under ice-cooling. The reaction solution is allowed to cool in a refrigerator overnight, and concentrated to dryness under reduced pressure. The resulting crystals are used in the subsequent reaction without purification.

(2) The above product is dissolved in anhydrous toluene (40 ml), and the mixture is refluxed for 15 hours. The reaction solution is concentrated to dryness under reduced pressure, and isopropanol is added to the residue. The precipitated crystals are collected by filtration, and recrystallized from methanol to give the desired compound as a colorless solid.

Using the corresponding starting compounds, the same procedure as Example 163 are repeated to give the following compounds of Examples 164–165.

Example 164

6-Benzyl-3-(5-ethoxy-1,2,4-oxadiazol-3-yl)-5,6,7,8-tetrahydro-1,6-naphthyridin-2(1H)-one

Example 165

6-Benzyl-3-(5-isopropoxy-1,2,4-oxadiazol-3-yl)-5,6,7,8-tetrahydro-1,6-naphthyridin-2(1H)-one

Example 166

Preparation of 6-benzyl-3-(3-methoxy-1,2,4-oxadiazol-5-yl)-5,6,7,8-tetrahydro-1,6-naphthyridin-2(1H)-one:

A suspension of N-methoxythiocarbonyl 6-benzyl-5,6,7,8-tetrahydro-2(1H)-oxo-1,6-naphthyridine-3-carboxyamide (3.6 g, 10 mmole) and hydroxylamine hydrochloride (1.4 g, 20 mmole) in pyridine (20 ml) is refluxed overnight. The reaction solution is concentrated to dryness under reduced pressure, and water is added to the residue. The precipitated crystals are collected by filtration, and recrystallized from methanol to give a colorless solid.

Using the corresponding starting compounds, the same procedures as Example 166 are repeated to give the following compounds of Examples 167–168.

Example 167

6-Benzyl-3-(3-ethoxy-1,2,4-oxadiazol-5-yl)-5,6,7,8-tetrahydro-1,6-naphthyridin-2(1H)-one

Example 168

6-Benzyl-3-(3-isopropoxy-1,2,4-oxadiazol-5-yl)-5,6,7,8-tetrahydro-1,6-naphthyridin-2(1H)-one

Reference Example 1

Preparation of 6-benzyl-5,6,7,8-tetrahydro-2(1H)-oxo-1,6-naphthyridine-3-carbohydrazide:

A solution of ethyl 6-benzyl-5,6,7,8-tetrahydro-2(1H)-oxo-1,6-naphthyridine-3-carboxylate (5.6 g, 18 mmole) and hydrazine monohydrate (2.7 g, 54 mmole) in ethanol (300 ml) is refluxed for 3 hours. After cooling, the precipitated crystals are collected by filtration, and recrystallized from ethanol to give a colorless solid (5.2 g).

Yield: 96.8%
m.p. 218°–220° C.

Reference Example 2

Preparation of 1-methyl-1-cyclopropanecarbohydrazide:

A mixture of ethyl 1-methyl-1-cyclopropanecarboxylate (10 g, 7.8 mmole) and hydrazine monohydrate (5.1 g, 0.1 mole) is heated with stirring at 100° C. for 4 hours. To the reaction solution is added toluene (50 ml), and the mixture is refluxed for 3 hours while distilling off water. After cooling, the precipitated crystals are collected by filtration, and washed with diisopropyl ether to give the desired compound (8.9 g) as a colorless crystal.

Yield: 99%
m.p. 85°–87° C.

Reference Example 3

Preparation of 6-benzyl-5,6,7,8-tetrahydro-2(1H)-oxo-1,6-naphthyridine-3-methanol:

A mixture of ethyl 6-benzyl-5,6,7,8-tetrahydro-2(1H)-oxo-1,6-naphthyridine-3-carboxylate (20 g, 64 mmole), tetramethylammonium borohydride (25 g, 97 mmole) and 1,2-dichloroethane (200 ml) is refluxed for 4 hours. The reaction solution is concentrated to dryness under reduced pressure. Water is added to the residue, and the mixture is refluxed overnight, and cooled with ice. The precipitated crystals are collected by filtration, and dried to give the desired compound.

Reference Example 4

Preparation of 6-benzyl-5,6,7,8-tetrahydro-2(1H)-oxo-1,6-naphthyridine-3-carbaldehyde:

To a solution of 6-benzyl-5,6,7,8-tetrahydro-2(1H)-oxo-1,6-naphthyridine-3-methanol (2.7 g, 10 mmole) in chloroform (100 ml) is added active manganese dioxide (13.5 g), and the mixture is refluxed for 5 hours. After cooling, the insoluble materials are removed by filtration, and the filtrate is concentrated to dryness under reduced pressure. The residue is purified by medium-pressure column chromatography of Diaion CHP-20P (solvent; acetonitrile and water, with concentration gradient) to give the desired compound.

Reference Example 5

Preparation of 6-benzyl-5,6,7,8-tetrahydro-2(1H)-oxo-1,6-naphthyridine-3-aldoxime:

A solution of 6-benzyl-5,6,7,8-tetrahydro-2(1H)-oxo-1,6-naphthyridine-3-carbaldehyde (5.4 g, 20 mmole) and hydroxylamine hydrochloride (2.8 g, 40 mmole) in ethanol (50 ml) is refluxed for 3 hours. After cooling, the precipitated crystals are collected by filtration, and dried to give the desired compound.

Reference Example 6

Preparation of 6-benzyl-5,6,7,8-tetrahydro-2(1H)-oxo-1,6-naphthyridine-3-hydroxyiminoyl chloride:

To a solution of 6-benzyl-5,6,7,8-tetrahydro-2(1H)-oxo-1,6-naphthyridine-3-aldoxime (2.8 g, 10 mmole) in DMF (30 ml) is added N-chlorosuccinimide (1.4 g, 10 mmole) in portions at room temperature, and the mixture is stirred for 5 hours. The reaction solution is poured into ice-water, and the precipitated crystals are collected by filtration, and dried to give the desired compound.

Reference Example 7

Preparation of 6-benzyl-5,6,7,8-tetrahydro-2(1H)-oxo-1,6-naphthyridine-3-azidoxime:

A mixture of 6-benzyl-5,6,7,8-tetrahydro-2(1H)-oxo-1,6-naphthyridine-3-hydroxyiminoyl chloride (3.2 g, 10 mmole), sodium azide (0.65 g, 10 mmole) and DMF (30 ml) is stirred at room temperature for 6 hours. The reaction solution is poured into ice-water, and the precipitated crystals are collected by filtration, and dried to give the desired compound.

Reference Example 8

Preparation of O-methoxycarbonyl 6-benzyl-5,6,7,8-tetrahydro-2(1H)-oxo-1,6-naphthyridine-3-azidoxime:

To a solution of 6-benzyl-5,6,7,8-tetrahydro-2(1H)-oxo-1,6-naphthyridine-3-azidoxime (3.2 g, 10 mmole) and triethylamine (1.1 g, 10 mmole) in dichloromethane (60 ml) is added dropwise with stirring a solution of methyl chloroformate (1.0 g, 10 mmole) in dichloromethane (5 ml) under ice-cooling. The mixture is warmed to room temperature, and stirred for 3 hours. The reaction solution is concentrated to dryness under reduced pressure, and water is added to the residue. The precipitated crystals are collected by filtration, and dried over to give the desired compound.

Reference Example 9

Preparation of 6-benzyl-5,6,7,8-tetrahydro-2(1H)-oxo-1,6-naphthyridine-3-carboisothiocyanate:

(1) To a solution of 6-benzyl-5,6,7,8-tetrahydro-2(1H)-oxo-1,6-naphthyridine-3-carboxylic acid hydrochloride (3.2 g, 10 mmole) and triethylamine (3.1 g, 30 mmole) in dichloromethane (50 ml) is added dropwise with stirring a solution of thionyl chloride (1.3 g, 10 mmole) in dichloromethane (5 ml) under ice-cooling. After the addition, the mixture is warmed to room temperature, and stirred for one hour, and is concentrated under reduced pressure to give an acid chloride as an oil.

(2) To a solution of the above oily product in 2N aqueous sodium hydroxide solution (25 ml) is added potassium thiocyanate (1.5 g, 15 mmole), and the mixture is stirred at room temperature for 20 hours. The mixture is extracted with chloroform, and the extract is dried over anhydrous sulfuric acid, and concentrated to dryness under reduced pressure. The residue is purified by silica gel column chromatography (solvent; chloroform:methanol=5:1) to give the desired compound as a colorless solid.

Reference Example 10

Preparation of N-methoxythiocarbonyl 6-benzyl-5,6,7,8-tetrahydro-2(1H)-oxo-1,6-naphthyridine-3-carboxamide:

To a solution of 6-benzyl-5,6,7,8-tetrahydro-2(1H)-oxo-1,6-naphthyridine-3-carboisothiocyanate (3.3 g, 10 mmole) in absolute methanol (30 ml) is added sodium methoxide (1.1 g, 20 mmole), and the mixture is refluxed for 20 hours. The reaction solution is concentrated under reduced pressure, and ethanol is added to the residue. The precipitated crystals are collected by filtration, and dried to give the desired compound.

| Preparation 1 Capsules: | |
|---|---|
| 6-Benzyl-3-(3-methoxy-1,3,4-oxadiazol-5-yl)-5,6,7,8-tetrahydro-1,6-naphthyridin-2(1H)-one | 5 g |
| Corn starch | 57 g |
| Lactose | 10 g |
| Crystalline cellulose | 25 g |
| Hydroxypropyl cellulose | 2 g |
| Light silicic anhydride | 0.5 g |
| Magnesium stearate | 0.5 g |

According to a conventional method, the above components are mixed and kneaded to give the granules, which are packed into 1000 capsules to give a capsule preparation (each 100 mg).

| Preparation 2 Tablets: | |
|---|---|
| 6-Benzyl-3-(3-methoxy-1,3,4-oxadiazol-5-yl)-5,6,7,8-tetrahydro-1,6-naphthyridin-2(1H)-one | 5 g |
| Corn starch | 20 g |
| Lactose | 30 g |
| Hydroxypropyl cellulose | 5 g |
| Low-substituted hydroxypropyl cellulose | 10 g |

According to a conventional method, the above components are mixed and kneaded, and thereto are added light silicic anhydride and magnesium stearate, and the mixture is tabletted to give tablets containing 10 mg of the active ingredient in each tablet.

| Preparation 3 Powders: | |
|---|---|
| 6-Benzyl-3-(3-methoxy-1,3,4-oxadiazol-5-yl)-5,6,7,8-tetrahydro-1,6-naphthyridin-2(1H)-one | 5 g |
| Corn starch | 173 g |
| Lactose | 300 g |
| Hydroxypropyl cellulose | 20 g |

According to a conventional method, the above components are mixed and kneaded, pulverized, and thereto is added light silicic anhydride (q.s.) to give 50-trituration.

What is claimed is:

1. A 3-oxadiazolyl-5,6,7,8-tetrahydro-1,6-naphthyridine derivative of the formula (I):

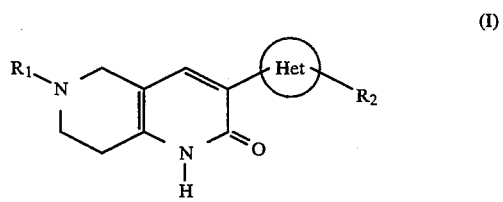

wherein Het is an oxadiazole ring, $R_1$ is hydrogen atom, an acyl group, a lower alkyl group or a group of the formula: —$CH_2R_1'$ (in which $R_1'$ is a cyclo-lower alkyl group, a lower alkenyl group, a lower alkynyl group, benzyl group, aryl group or a heteroaromatic group), $R_2$ is a lower alkyl group, a cyclo-lower alkyl group, a lower alkenyl group, a lower alkynyl group, aryl group, a heteroaromatic group, a halogeno-lower alkyl group, a lower alkoxy-lower alkyl group, a lower alkoxy group, a lower alkenyloxy group, a phenoxy group or a lower alkylthio group, or a pharmaceutically acceptable acid addition salt thereof.

2. The compound according to claim 1, wherein $R_1$ is a group of the formula: —$CH_2R_1'$ (in which $R_1'$ is phenyl group, a substituted phenyl group, or a 5-membered heteroaromatic group), $R_2$ is a lower alkyl group, a cyclo-lower alkyl group, a lower alkenyl group phenyl group or a substituted phenyl group, a 5-membered heteroaromatic group or a lower alkoxy group, or a pharmaceutically acceptable acid addition salt thereof.

3. The compound according to claim 2, wherein $R_2$ is an alkyl group having 1 to 3 carbon atoms, cyclopropyl group, or an alkoxy group having 1 to 3 carbon atoms, or a pharmaceutically acceptable acid addition salt thereof.

4. The compound according to claim 3, wherein Het is 1,3,4-oxadiazole ring, or a pharmaceutically acceptable acid addition salt thereof.

5. The compound according to claim 3, wherein Het is 1,2,4-oxadiazole ring, or a pharmaceutically acceptable acid addition salt thereof.

6. The compound according to claim 4, which is 6-benzyl-3-(5-methoxy-1,3,4-oxadiazol-2-yl)-5,6,7,8-tetrahydro-1,6-naphthyridin-2(1H)-one, or a pharmaceutically acceptable acid addition salt thereof.

7. The compound according to claim 4, which is 6-(2-chlorobenzyl)-3-(5-methoxy-1,3,4-oxadiazol-2-yl)-

5,6,7,8-tetrahydro-1,6-naphthyridin-2(1H)-one, or a pharmaceutically acceptable acid addition salt thereof.

8. The compound according to claim 4, which is 6-(4-chlorobenzyl)-3-(5-methoxy-1,3,4-oxadiazol-2-yl)-5,6,7,8-tetrahydro-1,6-naphthyridin-2(1H)-one, or a pharmaceutically acceptable acid addition salt thereof.

9. The compound according to claim 4, which is b 6-(2-bromobenzyl)-3-(5-methoxy-1,3,4-oxadiazol-2-yl)-5,6,7,8-tetrahydro-1,6-naphthyridin-2(1H)-one, or a pharmaceutically acceptable acid addition salt thereof.

10. The compound according to claim 4, which is 6-(2-chloro-5-fluorobenzyl)-3-(5-methoxy-1,3,4-oxadiazol-2-yl)-5,6,7,8-tetrahydro-1,6-naphthyridin-2(1H)-one, or a pharmaceutically acceptable acid addition salt thereof.

11. The compound according to claim 4, which is 6-(2-bromo-5-fluorobenzyl)-3-(5-methoxy-1,3,4-oxadiazol-2-yl)5,6,7,8-tetrahydro-1,6-naphthyridin-2(1H)-one, or a pharmaceutically acceptable acid addition salt thereof.

12. The compound according to claim 4, which is 6-benzyl-3-(5-cyclopropyl-1,3,4-oxadiazol-2-yl)-5,6,7,8-tetrahydro-1,6-naphthyridin-2(1H)-one, or a pharmaceutically acceptable acid addition salt thereof.

13. The compound according to claim 4, which is 6-benzyl-3-(5-ethyl-1,3,4-oxadiazol-2-yl)-5,6,7,8-tetrahydro-1,6-naphthyridin-2(1H)-one, or a pharmaceutically acceptable acid addition salt thereof.

14. The compound according to claim 4, which is 6-benzyl-3-(5-isopropyl-1,3,4-oxadiazol-2-yl)-5,6,7,8-tetrahydro-1,6-naphthyridin-2(1H)-one, or a pharmaceutically acceptable acid addition salt thereof.

15. The compound according to claim 5, which is 6-benzyl-3-(5-cyclopropyl-1,2,4-oxadiazol-3-yl)-5,6,7,8-tetrahydro-1,6-naphthyridin-2(1H)-one, or a pharmaceutically acceptable acid addition salt thereof.

16. The compound according to claim 5, which is 6-benzyl-3-(5-methyl-1,2,4-oxadiazol-3-yl)-5,6,7,8-tetrahydro-1,6-naphthyridin-2(1H)-one, or a pharmaceutically acceptable acid addition salt thereof.

17. The compound according to claim 5, which is 6-benzyl-3-(5-ethyl-1,2,4-oxadiazol-3-yl)-5,6,7,8-tetrahydro-1,6-naphthyridin-2(1H)-one, or a pharmaceutically acceptable acid addition salt thereof.

18. The compound according to claim 5, which is 6-benzyl-3-(3-methyl-1,2,4-oxadiazol-5-yl)-5,6,7,8-tetrahydro-1,6-naphthyridin-2(1H)-one, or a pharmaceutically acceptable acid addition salt thereof.

* * * * *

UNITED STATES PATENT AND TRADEMARK OFFICE
CERTIFICATE OF CORRECTION

PATENT NO. : 5,367,078
DATED : November 22, 1994
INVENTOR(S) : Kazunori OHNO et al.

It is certified that error appears in the above-indentified patent and that said Letters Patent is hereby corrected as shown below:

In the Abstract on the cover page, the last two lines, change "benzodiazedine" to --benzodiazepine--.

Column 1, line 19, change "have" to --having--.

Column 2, line 61, change "realate" to --malate--.

Column 4, line 47, change "after-the" to --after the--;

line 65, change "above;," to --above,--.

Column 5, line 46, change "does," to --does--.

Column 6, line 20, change "staffing" to --starting--.

Column 14, line 47, change "salts. For" to --salts, for--;

line 58, change "ones;" to --ones--.

Column 16, line 19, change "real" to --mal--.

Column 20, line 36, change "naphthyridine-" to --naphthyridin- --.

UNITED STATES PATENT AND TRADEMARK OFFICE
CERTIFICATE OF CORRECTION

PATENT NO. : 5,367,078
DATED : November 22, 1994
INVENTOR(S) : Kazunori OHNO et al.

It is certified that error appears in the above-indentified patent and that said Letters Patent is hereby corrected as shown below:

Column 44, line 46, change "when" to --then--.

Column 57, line 1 of claim 9, after "which is" delete --b--.

line 3 of claim 11, change "-2-yl)5,6,7,8-" to -- -2-yl)-5,6,7,8- --.

Signed and Sealed this

Fourth Day of April, 1995

Attest:

BRUCE LEHMAN

*Attesting Officer*    *Commissioner of Patents and Trademarks*